United States Patent
Saini et al.

(10) Patent No.: US 10,976,294 B2
(45) Date of Patent: Apr. 13, 2021

(54) TECHNIQUES FOR TOXIC METAL DETECTION AND SPECIATION IN AQUEOUS MATRICES

(71) Applicant: AMS Trace Metals, Inc., Wilmington, DE (US)

(72) Inventors: Harmesh K. Saini, Santa Clara, CA (US); Vladimir Dozortsev, Ridgewood, NJ (US)

(73) Assignee: AMS Trace Metals, Inc., Wilmington, DE (US)

( * ) Notice: Subject to any disclaimer, the term of this patent is extended or adjusted under 35 U.S.C. 154(b) by 170 days.

(21) Appl. No.: 16/309,009

(22) PCT Filed: Jun. 16, 2017

(86) PCT No.: PCT/US2017/038022
§ 371 (c)(1),
(2) Date: Dec. 11, 2018

(87) PCT Pub. No.: WO2018/013293
PCT Pub. Date: Jan. 18, 2018

(65) Prior Publication Data
US 2020/0003745 A1 Jan. 2, 2020

Related U.S. Application Data

(60) Provisional application No. 62/361,923, filed on Jul. 13, 2016.

(51) Int. Cl.
*G01N 33/18* (2006.01)
*G01N 1/40* (2006.01)
(Continued)

(52) U.S. Cl.
CPC ......... *G01N 33/1813* (2013.01); *B03C 1/282* (2013.01); *B03C 1/286* (2013.01);
(Continued)

(58) Field of Classification Search
CPC .... G01N 1/4044; G01N 1/44; G01N 33/2858; G01N 15/04; G01N 15/0656; B03C 1/282; B03C 1/286
(Continued)

(56) References Cited

U.S. PATENT DOCUMENTS

| | | | | |
|---|---|---|---|---|
| 4,957,593 | A * | 9/1990 | Shaw | C25B 11/04 204/291 |
| 7,531,134 | B1 * | 5/2009 | Anderson | B01D 59/44 250/281 |

(Continued)

OTHER PUBLICATIONS

ISR/WO mailed Sep. 6, 2017 in PCT/US2017/038022 (the international application corresponding to this application), 9 pages.
(Continued)

*Primary Examiner* — Clayton E. LaBalle
*Assistant Examiner* — Kevin C Butler
(74) *Attorney, Agent, or Firm* — Marc P. Schuyler

(57) ABSTRACT

An in-situ measurement apparatus automatically draws aqueous samples on an intermittent or ad-hoc basis and measures specific metal specie concentration. The apparatus can perform both raw measurement of specific metal specie, as well as processing to convert other species of the same metal to the specific metal specie or to destroy or remove unwanted masking agents (e.g. organics). In one application, "dirty" water from a scrubber is measured for Se(IV) presence (using a renewable voltametric system), both with and without the masking agents present; in addition, selective processing converts other selenium species to Se(IV), permitting assessment of total selenium and measurement of Se(VI) presence. Automated reactions can then be taken to remove detected toxic substances from waste water without excess reliance on treatment chemicals, and so as to ensure that only water complaint with regulatory standards is released into the environment.

22 Claims, 7 Drawing Sheets

(51) Int. Cl.
*G01N 1/44* (2006.01)
*G01N 15/06* (2006.01)
*B03C 1/28* (2006.01)
*G01N 15/04* (2006.01)
*G01N 33/28* (2006.01)

(52) U.S. Cl.
CPC .............. *G01N 1/4044* (2013.01); *G01N 1/44* (2013.01); *G01N 15/04* (2013.01); *G01N 15/0656* (2013.01); *G01N 33/2858* (2013.01)

(58) Field of Classification Search
USPC ........................................................ 73/61.42
See application file for complete search history.

(56) References Cited

U.S. PATENT DOCUMENTS 7,815,801 B2 * 10/2010 Borg ........................ C12N 1/26
  210/610

2014/0260708 A1 * 9/2014 Harrell ............... G01N 33/2823
  73/866

OTHER PUBLICATIONS

Cooper et al., "Wastewater Treatment for Flue Gas Desulfurization (FGD) at Electric Power Plants" (white paper downloaded Jul. 1, 2016), 8 pages.
"Hydride Generation vs. IC-ICP-MS for Selenium Speciation Analysis: A side-by-side comparison," Applied Speciaton and Consulting, 2 pages (brochure downloaded Jul. 1, 2016).
"Trace Arsenic and Selenium Analysis," Applied Speciation and Consulting, 2 pages (brochure downloaded Jul. 1, 2016).
"Treatment Plant Optimization for Removal of Trace Metals," Applied Speciaton and Consulting, 2 pages (brochure downloaded Jul. 1, 2016).
"Selenium Speciation in FGD Plant Effluents," Applied Speciation and Consulting, 2 pages (brochure downloaded Jul. 1, 2016).

* cited by examiner

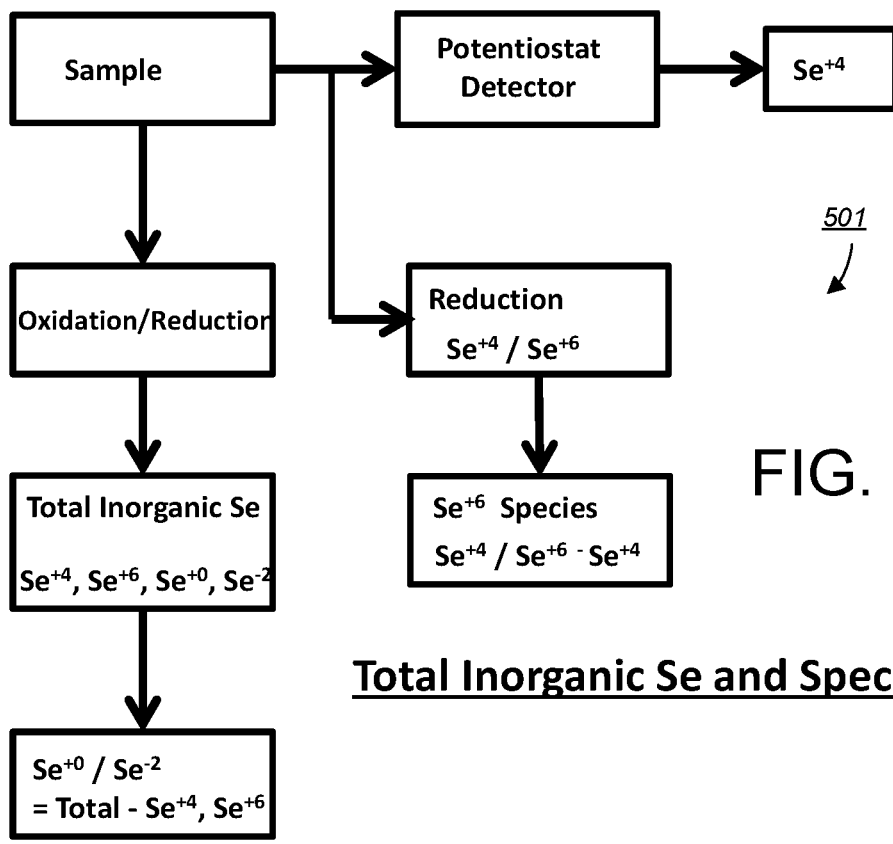
Total Inorganic Se and Speciation
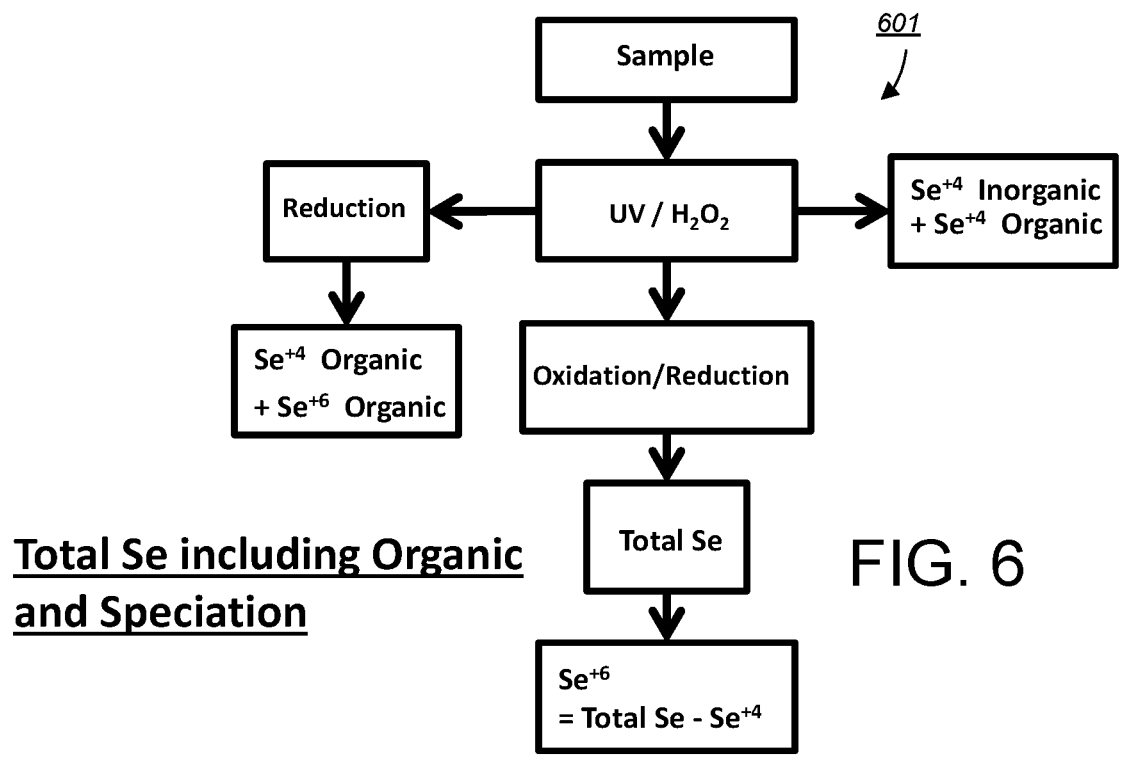
Total Se including Organic and Speciation

TECHNIQUES FOR TOXIC METAL DETECTION AND SPECIATION IN AQUEOUS MATRICES

This application claims the benefit of U.S. Provisional Patent Application No. 62/361,923, filed on Jul. 13, 2016 on behalf of first-named inventor Harmesh K. Saini for "Techniques For Toxic Metal Detection And Speciation In Waste Water And In Treated Water," which is hereby incorporated by reference. This application also incorporates by reference PCT Publication WO2016174526 (Patent Cooperation Treaty Application No. PCT/IB2016/000776, filed on Apr. 27, 2016 for Renewable Mercury Meniscus Electrode With Mercury Circulation System And Contaminant Removal).

The present disclosure relates to methods, devices and systems for identifying toxic metal presence in liquids; more specifically, the present disclosure provides techniques for toxic metal speciation in aqueous matrices, such as raw water, potable water, waste water and/or treated water, notwithstanding the presence of organics and other waste materials that create measurement noise which would otherwise interfere with measurement accuracy.

BACKGROUND

Many industrial processes produce toxic waste materials which must be safely disposed of. One prime example relates to the use of scrubbers for flue gas desulfurization, which attempt to remove sulfur and other substances produced in exhaust gasses as a by-product of burning coal. While many by-products (such as gypsum) can be extracted and recycled to other purposes, other materials are more toxic and must be safely isolated and disposed of. As one non-limiting example, some processes produce waste water which suspend soluble toxic metals dangerous to human health and aquatic life, as well as other types of organics and inorganics; this water cannot be recycled or dumped until the dangerous substances are removed, typically through processes that precipitate these substances as insoluble sludge, which is then isolated from the "treated" water. The precipitates can be formed by treating the waste water with specific amounts of specific chemicals, generally specifically tailored to the type and quantity of waste material to be removed. Optionally, the treated water can be retested to ensure appropriate reduction of the toxic substances.

As this discussion implies, in order to reduce identified toxins to safe levels, it is typically desired to first test waste water to identify substances present and the concentration of those substances. This is no easy task, considering that the constantly-changing spectrum of materials present and their respective concentrations can create measurement noise or otherwise make it difficult to obtain a true understanding of materials present; organic materials in particular, can from a measurement perspective mask the presence of certain harmful metals. Rough testing methods do exist, for example, that involve sample preparation steps like digesting and heating the samples over lengthy periods of time to evaporate substances that mask metal presence; unfortunately, such preparation processes take too long and can often evaporate and/or change speciation of the substances being measured, i.e., the results take too long and can be inaccurate. It is also sometimes possible to perform laboratory testing, for example, with equipment that performs very fine filtration or other sample processing in order to remove some substances (e.g., certain organics); this filtration then permits ensuing use of an Inductively Coupled Plasma Mass Spectroscopy (ICP-MS) in order to isolate and measure concentration of substances of interest. However, such testing is expensive, can take many hours or days, and it typically requires removal of waste water samples to a laboratory having the necessary equipment. The required filtration and/or digestion processes can be extensive, and without proper premeasurement processing, the complex organics present can degrade the laboratory's ICP-MS equipment; for this reason, some laboratories will even refuse to perform this type of testing. The excessive time required to obtain accurate ICP-MS results, in turn, makes it difficult to obtain a real-time understanding of waste water constituency, as water composition may have changed by the time laboratory results are available. Thus, in summary, conventional testing typically takes too long and, all too often, excess chemical treatments are performed in order to be completely sure that all toxic substances have been removed.

Historically, metal ion analysis in water samples has been dominated by quantifying total metal content, while metal ion speciation has been broadly neglected. However, metal speciation in natural waters, drinking water and industrial process waters can be quite important, depending on the type of metal, because toxicity, bioavailability, environmental mobility, biogeochemical behavior, and potential risk in general are strongly dependent on the chemical species of metals. Chromium can be used as a representative example: While trivalent chromium Cr(III) is a nutrient for human body, hexavalent chromium Cr(VI) specie is a highly toxic carcinogen even at trace levels. It therefore can be important to have an understanding of both total metal concentration (for a specific metal), as well as concentration of various species of that metal. In the case of chromium, both total chromium and hexavalent chromium should be tightly monitored and controlled in water supply systems. In addition, successful remediation of some toxic metalloids from different water sources strongly depends on precise knowledge on their speciation, because different species of the same element present in the water sample may respond differently to different treatment processes. Metal speciation at trace levels is a difficult and challenging task even for certified analytical labs and it requires sophisticated equipment and well trained personnel. In case of selenium, different species of the metalloid present in water should be completely converted into the single form suitable for remediation form, and high remediation process stability cannot be achieved without timely and accurate information on selenium speciation results at different process stages.

What are needed are techniques for rapid, in-situ measurement of waste water contaminants, particularly certain types of toxic metals (and their associated species). Such techniques, if usable in the field, would enable accurate measurement of waste water contaminants, identification of suitable treatments to remove those contaminants, and more efficient, sparing use of chemical treatments. The present invention addresses these needs and presents further, related advantages.

BRIEF DESCRIPTION OF THE DRAWINGS

FIG. 3 exemplifies these techniques as applied to the measurement of specific selenium species.

FIG. 5 is a block diagram showing techniques for processing a water sample to identify total inorganic selenium in waste water, and associated speciation.

FIG. 6 is a block diagram showing techniques for processing a water sample to identify total organic and inorganic selenium in waste water, and associated speciation.

Figure 1:
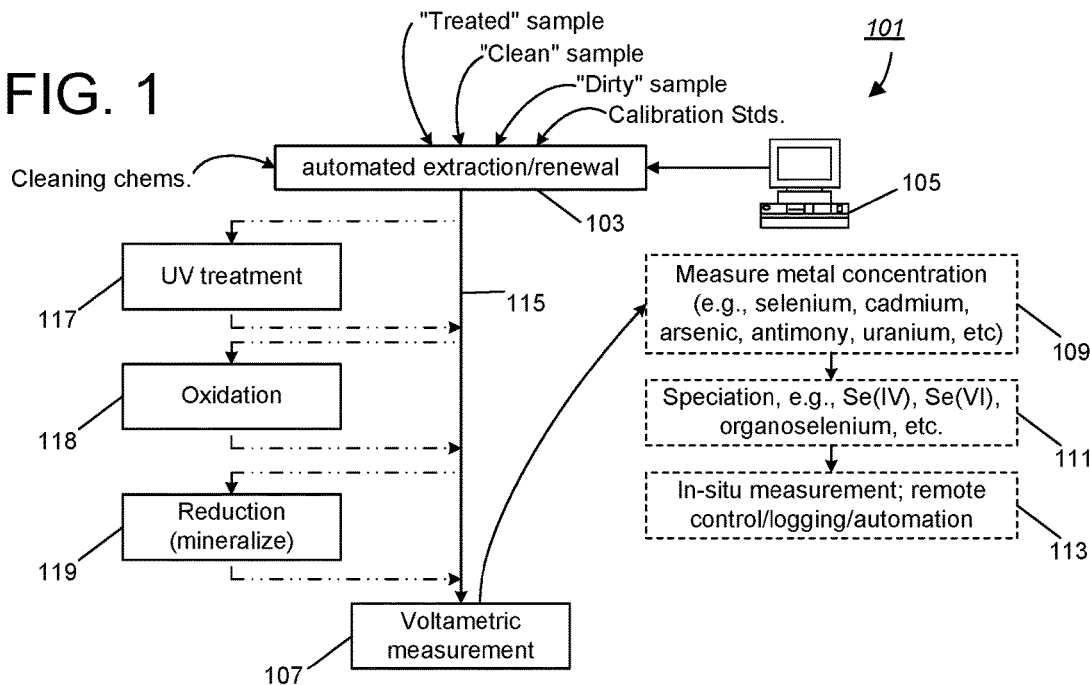
FIG. 1 is a block diagram showing techniques for toxic metal detection and speciation in water samples (including "treated" and/or "clean" and/or "dirty" water samples, as depicted in the FIG.).

The subject matter defined by the enumerated claims may be better understood by referring to the following detailed description, which should be read in conjunction with the accompanying drawings. This description of one or more particular embodiments, set out below to enable one to build and use various implementations of the technology set forth by the claims, is not intended to limit the enumerated claims, but to exemplify their application. Without limiting the foregoing, this disclosure provides several different examples of techniques used to measure toxic metal presence in aqueous matrices, especially including "dirty" water produced by a waste water system. The disclosed techniques provide for measurement methodologies which can provide far more accurate results than conventional processes; the disclosed methodologies can be performed, in-situ, on a near real-time basis, and can process waste water and/or treated water samples that would not be suitable for ICP-MS based laboratory testing. The various techniques can also be embodied as software for performing these techniques, or in the form of a computer, network or other device running such software, or as stored data sets produced as the product of such analysis. While specific examples are presented, the principles described herein may also be applied to other methods, components, devices, systems and applications as well.

DETAILED DESCRIPTION

Several of the embodiments presented in this disclosure provide for systems, methods, devices and techniques for measuring toxic metal presence in aqueous matrices; these matrices can include, without limitation, raw water, potable water, waste water, treated water. Optionally, the water is waste water produced by industrial processes (e.g. coal power plants) that rely on the burning of fossil fuels (e.g., coal or other organics). The disclosed techniques optionally use a system having a number of components or subsystems that can be used in various combinations and permutations, under automated processor control; in one contemplated optional implementation, these various components or subsystems are used both on a pipelined basis (for certain measurements) as well as a parallel basis (for other measurements), providing a measurement cycle on the order of an hour instead of days. One of these components or subsystems can include a voltametric measurement device with a renewable electrode, for example, as described in the aforementioned patent application No. PCT/IB2016/000776 (published as WO2016174526, and incorporated herein by reference). Optional use of these various ones of these components or subsystems together can provide for automated, remote monitoring and for accurate real-time results for of measurement (i.e., which otherwise might only be accurately measured through extensive sample preparation and ICP-MS processes, as referenced previously). The optional, described components/subsystems provide for monitoring of toxic metal presence in aqueous matrices with little to no maintenance, other than periodic consumables disposal and replenishment. As should be apparent, these techniques provide for substantial improvement in ability to continuously monitor a water supply, optionally on a remote basis, requiring little to no human involvement. The disclosed techniques provide for substantial advancement in the field of aqua metrology.

In one non-limiting, exemplary application, a measurement system for toxic metals is deployed in a processing facility that relies on flue gas desulfurization, for example, a coal-fired power plant. Flue gas desulfurization processes use "scrubbers" to recycle sulfur and other compounds from exhaust gases and use water to remove toxic metals either from these scrubbers or directly from the exhaust gasses. The waste water produced from such processes can be a complex chemical mixture, having numerous organic compounds and toxic metals, such as selenium, cadmium, lead, copper, arsenic, chromium, beryllium, aluminum, nickel, uranium, selenium, zinc and other metals. The system described below can be applied in-line in such a system to take remote, automated measurements (e.g., every 2-6 hours, or on another desired basis) of the dirty water; extracted "dirty" water is held in a sample reservoir, and then subjected to a series of measurements pertinent to each metal which is to be detected. For example, a small sample (e.g., subsample) can be drawn from the reservoir and used to detect selenium presence and speciation; the system can then be used to detect uranium presence and speciation, and so on. Alternatively, multiple such systems can be used together, in parallel to one another, to perform these respective processes. Not only is metal presence detected, but associated speciation is identified, along with associated concentrations. To cite on specific example that will be used in the ensuing discussion, in one mode of operation, the system detects and discriminates Selenite (i.e., "Se(IV)" or $Se^{4+}$) from Selenate (i.e., "Se(VI)" or $Se^{6+}$) from various organic compounds having selenium ("organoselenium"), and so forth. The result of the measurement cycle is an understanding of specific concentrations of these various species in the waste water. Armed with this information, control systems provided by this disclosure optionally then cause the release of treatment chemicals into the water supply, in exactly the proper amounts, so as to make the various harmful metal species insoluble, as described earlier. Optionally, the detection system can then be reused (or a second detection system can be used) to remeasure treated water to confirm that toxic metals have been reduced to acceptable safe levels, with additional treatment cycles performed (or other actions taken) as necessary. Note that these specific processes, matrices of interest and actions taken are optional and illustrative, e.g., in a variation, precise treatment chemicals and quantities of those chemicals are computed and fed out to a human operator, who then manually adds (or controls other systems to add) the pertinent treatment chemicals. As should be apparent, these processes permit far more efficient treatment of aqueous matrices (a) by adding only the proper amount of treatment chemicals, thereby saving substantial time and money in recycling, and (b) by accurately measuring toxic metal presence, so as to permit precise comparison with specific limits, such that harmful metals are not released into the environment as a soluble component of inadequately treated waste. Naturally, it is also possible simply to use the measurement system to measure any desired individual species, with consequent reactions being optional.

As used herein, the term "metals" refers to traditional metals and metalloids as well as other elements that behave like metals and are sometimes referred to as toxic metals, for instance, selenium. Without limiting the foregoing, "toxic metals" as referred to herein can refer to toxic compounds that have as elements non-metals, alkali metals, transitional metals, alkaline metals, metalloids, rare earth elements, or other metals. Also, specifically contemplated implementations can feature instructions stored on non-transitory machine-readable media. Such instructional logic can be written or designed in a manner that has certain structure (architectural features) such that, when the instructions are ultimately executed, they cause the one or more general purpose machines (e.g., a processor, computer or other machine) to behave as a special purpose machine, having structure that necessarily performs described tasks on input operands in dependence on the instructions to take specific actions or otherwise produce specific outputs. "Non-transitory" machine-readable or processor-accessible "media" or "storage" as used herein means any tangible (i.e., physical) storage medium, irrespective of how data on that medium is stored, including without limitation, random access memory, hard disk memory, storage cards, optical memory, a disk-based memory (e.g., a hard drive, DVD or CD), server storage, volatile memory and/or other tangible mechanisms where instructions may subsequently be retrieved and used to control a machine. The media or storage can be in standalone form (e.g., a program disk or solid state device) or embodied as part of a larger mechanism, for example, a laptop computer, portable device, server, network, printer, or other set of one or more devices. The instructions can be implemented in different formats, for example, as metadata that when called is effective to invoke a certain action, as Java code or scripting, as code written in a specific programming language (e.g., as C++ code), as a processor-specific instruction set, or in some other form or language; the instructions can also be executed by a single, common processor or by different processors or processor cores, depending on embodiment. Throughout this disclosure, various processes will be described, any of which can generally be implemented as instructions stored on non-transitory machine-readable media. Also depending on implementation, the instructions can be executed by a single computer and, in other cases, can be stored and/or executed on a distributed basis, e.g., using one or more servers, web clients, or application-specific devices. Each function mentioned in reference to the various FIGS. herein can be implemented as part of a combined program or as a stand-alone module, either stored together on a single media expression (e.g., single floppy disk) or on multiple, separate storage devices. Also, various processes will be described herein, any of which can generally be implemented as instructional logic (e.g., as instructions stored on non-transitory machine-readable media), as hardware logic, or as a combination of these things, depending on embodiment or specific design. "Module" as used herein refers to a structure dedicated to a specific function; for example, a "first module" to perform a first specific function and a "second module" to perform a second specific function, when used in the context of instructions (e.g., computer code), refers to mutually-exclusive code sets. When used in the context of mechanical or electromechanical structures (e.g., an "encryption module," it refers to a dedicated set of components which might include hardware and/or software). In all cases, the term "module" is used to refer to a specific structure for performing a function or operation that would be understood by one of ordinary skill in the art to which the subject matter pertains as a conventional structure used in the specific art (e.g., a software module or hardware module), and not as a generic placeholder or "means" for "any structure whatsoever" (e.g., "a team of oxen") for performing a recited function. An "aqueous matrix," as used herein, can refer to any liquid medium, including without limitation, water. "Raw water" or "clean water" as used herein refers to water that has not been treated irrespective of its potability, for example, water from a lake or river of unknown composition. "Waste water" or "dirty water" refers to water produced as a by-product of an industrial, manufacturing, agricultural or other process, for example, where a waste material of some type is added to or carried away with water as a result of such process. "Treated water" refers to water that has deliberately received some type of chemical, optical, physical or other treatment to change its composition, for example, via the addition of a sanitizer (such as chlorine) or other chemicals, via ultraviolet light treatment, for example, to remove pathogens or waste materials. "Potable water" refers to water that is safe for human consumption. In all cases, it should be understood that techniques described herein can optionally be applied to each of these types of water, as well as to liquids other than water.

FIG. 1 provides a block diagram of one embodiment of a measurement system and its associated operation, which are generally designated using numeral 101. More specifically, an automated extraction system 103 is coupled to receive one of several solutions, optionally in this example including a "treated" water sample, a "clean" or "raw" water sample, a "dirty" water sample, and various calibration standards, as indicated in the FIG. The system in one optional embodiment is also a "renewable" system, meaning that it can also receive various cleaning chemicals such that the system can be automatically prepared for ensuing measurements, with additional, new samples being drawn and measured later, as water supply conditions change. The system is optionally controlled by a computer or processor, denoted by numeral 105, to perform these various functions either on an ad hoc basis or a prearranged basis (e.g., "every 6 hours").

As referenced earlier, such a system can optionally feature a voltametric measurement subsystem 107. Such a system typically uses a catalyst relevant to the substance (i.e., metal species) being measured, in a manner that causes the metals or metal species to migrate under the presence of electrical influence to an electrode; resultant current and/or voltage measurement is then used to measure concentration of the metal or metal species of interest. In one embodiment, described further below, such a system can optionally also feature a preconcentration column to extract one or more metals or metal species of interest, via a solid phase ion extraction process. The metals or metal species are then eluted from this medium using eluent solution and measured, to precisely detect total metal/metal species concentrations (109). The processes can be used to measure concentrations of individual toxic metals harmful to human health or the environment (109), such as selenium, cadmium, arsenic, chromium, lead, antimony, and uranium and other metals mentioned herein. Such processes are especially useful to measure speciation of toxic metals and other metals with multiple different states or species, such as by measuring total selenium concentration and/or other individual selenium species, such as Se(IV), Se(VI) and organoselenium presence (111). Use of these processes, with optional use of a low-maintenance, renewable electrode voltametric measurement system, provides for an in-situ device that can compute total metal and/or individual metal species concentrations in near real-time, optionally on an automated, remote basis, with automatic logging of results if desired (113).

As noted above, the described system can be used to measure speciation in "treated," "clean" or "dirty" water samples. For example, in one process described below, Se(IV) and Se(VI) can simultaneously be extracted and individually eluted from a solid-phase extraction medium, using 0.1 molar (M) hydrochloric acid (HCL) and using 3.0M HCL in sequential processes, and then measured in respective cycles, to permit individual, direct, toxic metal species concentration detection. Note that it might not always be advantageous to use preconcentration for "dirty" water samples, e.g., polymers and other organics in such a sample could potentially degrade the preconcentration column. In many applications, therefore, a preconcentration column is not used for dirty water samples, and different processes are used to enable individual toxic metal speciation in "dirty" water.

FIG. 1 shows a number of these processes, which can be performed using combinations and permutations of optional components or subsystems, as referenced earlier. For example, per numeral 115, a water sample can be provided directly to the voltametric measurement system 107—in the case of a "dirty" water sample, preconcentration is not used, and the voltametric measurement system is used to measure presence of an individual species, e.g., using chemistry that permits detection of concentration of Se(IV) (or another metal species); note that because there is no special processing of the sample before species detection that the results might be masked by the presence of various organics in the measurement sample. Nevertheless, such a measurement can be useful, for example, to identify the amount of masking that is taking place (relative to results of additional measurements, as referenced below). It is also possible to subject the sample, in lieu of path 115, to an ultraviolet (UV) light treatment using a system component for this purpose, as referenced by numeral 117. For example, optional processes described below use a 250 nanometer (250 nm) wavelength source with optional processes applied to enhance the efficiency of this process and provide for a short exposure time. The UV process breaks down the polymers and other organics that mask metal species detection, providing ability for the voltametric system to measure unmasked species presence (which as just referenced, permits identification of the degree of masking that takes place by reference to masked measurements). Advantageously, software running on the PC or processor 105 automatically makes this determination and stores results in non-transitory storage. Alternatively, or in addition, the sample can be mixed with an oxidizer (e.g., a $H_2O_2$ solution) which oxidizes organometals to convert them to inorganic forms suitable for measurement, per numeral 118. For example, the sample can be oxidized by the $H_2O_2$ solution, to convert for example organoselenium to Se(VI), which can then be measured by other processes. Further, the system can also instead or in addition to any of these processes subject the sample to a reduction process, e.g. by injecting hydrochloric acid into the sample (e.g., a 3.0M to 12M solution) and can further then heat the sample following suitable mixing—such process mineralizes selenium, essentially converting Se(VI) to Se(IV). By measuring Se(IV) presence using the mentioned voltametric process (e.g., using copper as a catalyst), one can measure without limitation each of (a) masked Se(IV) presence, (b) unmasked Se(IV) presence, (c) total Se presence (masked and/or unmasked, i.e., organoselenium is broken down and then the HCl/heating process is applied to convert all selenium to Se(IV), which then measured), (d) total Se(VI) presence (i.e., Se(IV) concentration is subtracted from total Se concentration to yield Se(IV) concentration, in iterations with and without conversion of organoselenium to Se(VI)), and (e) organoselenium presence by differentiating measurement results from (d). Advantageously, these computations and automated control of the measurement processes are performed by software running on computer/processor 105, as described earlier, with results logged, displayed to a human operator, or otherwise applied by computer/processor 105 in the form of automated systems control (e.g., to automatically treat a water supply). It is also possible to generate alarms, should excess species be detected (e.g., should toxic metal concentration in "recycled water" exceed safe limits). In one embodiment, by understanding precisely which species are present, and in which concentrations, exactly the correct amount of treatment chemicals can be added to the water supply to precipitate desired species from the "dirty" water. For example, a first treatment process can be applied to remove Se(IV), a second (different) treatment process can be applied to remove Se(VI), and yet another process can be applied to treat various forms of organoselenium.

Note again that reference to selenium and its various forms is exemplary only; that is, the described processes as noted earlier are useful to measuring many different metals and their various species, including without limitation any toxic metal, e.g., various forms of selenium, cadmium, arsenic, chromium, antimony, and uranium. Additional, while water has been exemplified as being the thing that is measured, the techniques described herein are not so limited, and the described processes can potentially be applied to any type of aqueous solution.

Figure 2:
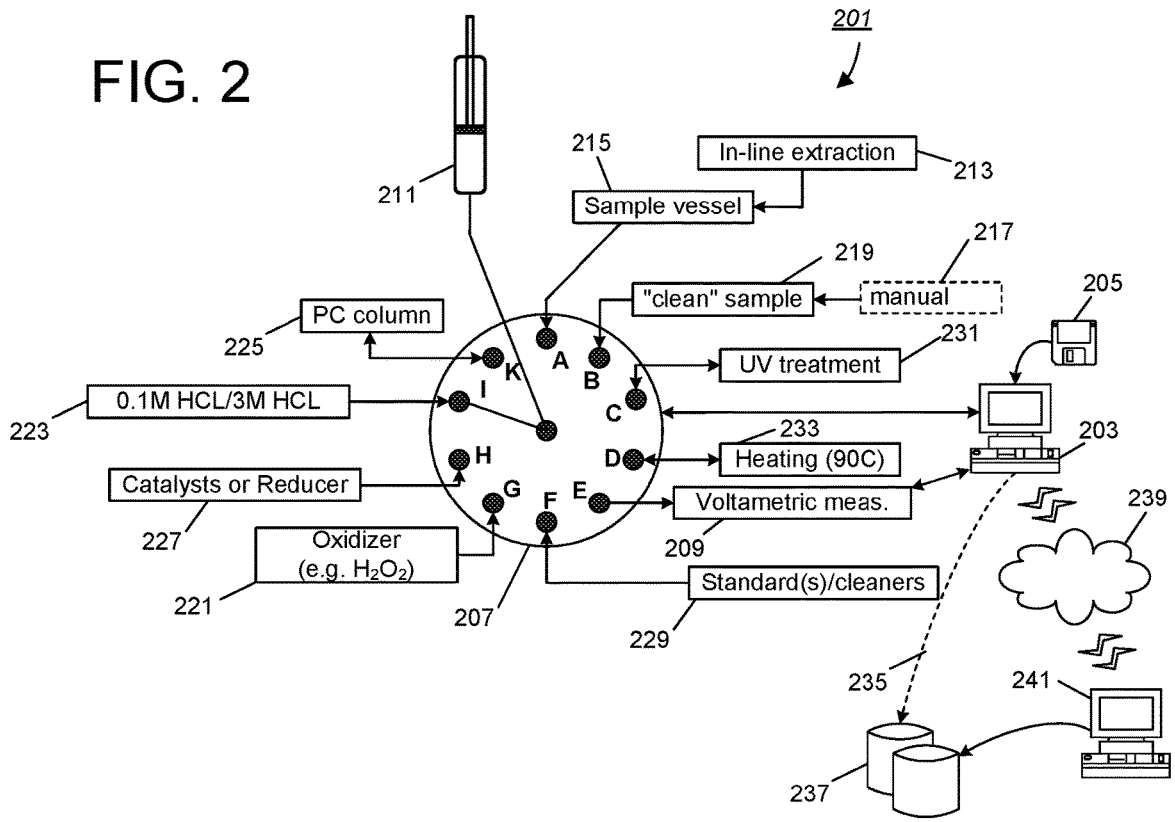
FIG. 2 is an illustrative block diagram showing configuration of an automated system for measuring toxic metal presence in water.

FIG. 2 provides additional detail on one embodiment for performing these various measurements, generally designated using numeral 201. Once again, all system components can optionally be controlled by a computer or processor (or one or more computers or processors, housed together or distributed) 203, operating under the control of suitable software (represented symbolically by a floppy disk icon 205). The system also uses a rotary selector 207, a voltametric measurement system 209 (as introduced above), a motion-controlled syringe and/or reaction vessel 211, and in-line extraction mechanism 213 and a sample vessel or reservoir 215. At ad hoc times or predetermined intervals, the control system (processors/computers/software) 203/205 cause the in-line extraction mechanism to draw a sample from the water supply (e.g., a treated or dirty water supply as referenced earlier), drawing, e.g., 50 mL of sample into the sample vessel or reservoir 215, from which individual measurement samples will then be drawn. The motion-controlled syringe 211 is then used for this purpose, for example, drawing a 5 mL subsample into the syringe 211. The motion-controlled syringe 211 can also be used to draw a "treated" sample 219 via an alternative input mechanism, for example, at the output of a water treatment facility, or to accept a manually-introduced sample, as referenced by numeral 217. Whichever sample is used, the motion-controlled syringe can then be used to draw and mix additional solutions, catalysts, reagents or other materials with the sample, transferring them to various system components as necessary; for example, the sample (mixed, previously processed, or otherwise) can be transferred to the voltametric system 209 (i.e., to a voltametric measurement cell). For example, the system can draw an oxidizer (e.g. $H_2O_2$), various catalysts (e.g., aqueous Cu), 0.1M/3.0M HCl, cleaning solutions and/or other substances into the syringe, using the syringe and associated conduits and aeration systems (see WO2016174526, which has been incorporated herein by reference) to mix these materials as necessary for ensuing processing steps, as variously indicated by numerals 221, 223, 227 and 229. The sample (mixed or otherwise) can for example be transferred to a UV treatment component 231 or a heating vessel 233. With each process, once processing is complete, the motion-controlled syringe 211 is used to transfer liquids to an ensuing vessel for other processing or for measurement; as an example, following UV treatment, a UV-treated liquid can be drawn back from UV treatment component 231 into the motion-controlled syringe 211 and, following adjustment of the rotary selector 207, can then be mixed with a reducer or catalyst (227) and transferred into the heating vessel 233 or the voltametric measurement cell (e.g., element 209), with a cleaner subsequently being used to rinse the syringe while measurement is being performed by the voltametric measurement component. Numeral 225 also references capability of the rotary selector 207 and syringe 211 to drive fluids into a preconcentration column 225, e.g., a clean water sample can be driven into this column to extract toxic metal species, with 0.1M and 3.0M HCL then being used in successive processes to elute different species from the column for corresponding successive measurements by the voltametric measurement component 207.

Reflecting back on the description thus far, it should be appreciated that the described architecture provides, in one embodiment, processes that can be performed in parallel, to enable real-time, in-situ measurements of multiple metal species. That is, the computer(s)/processor(s) 203 and/or system software 205 are advantageously designed to perform various different measurements in parallel, and so to complete measurements for any given metal in a measurement cycle that takes on the order of an hour of time or less. For example, while one sample is being processed by the UV treatment component 231, a different sample can be in voltametric measurement cell 209 and subject to voltametric measurement and, similarly, these processes can be interleaved and/or stacked against use of the preconcentration column 225 and/or use of the heating vessel 233. The following steps provide one example of how this can be done: (a) a "dirty" water subsample is injected into the voltametric measurement cell and is subjected to a first measurement; (b) immediately following this injection, and while measurement is occurring, a second "dirty" water subsample is moved using the syringe into the UV treatment component 231 and is subjected to a 15-minute UV processing cycle; (c) immediately following this movement, yet another (third) "dirty" water sample is drawn into the syringe with a reducer (e.g. 3.0 to 12M HCl), is mixed, and is injected into the heating vessel 233 for a 20 minute heat treatment at 90 degrees Centigrade, so as to mineralize metal from this third subsample; (d) following this process, the syringe is rinsed and, while other processes are occurring, is further used to draw a "treated" water sample and inject it into the PC column 225 for solid-phase transfer of ionic species; (e) other concurrent operations can also be performed and/or interleaved with any of the various steps described by this disclosure. Perhaps otherwise stated, through efficient systems control, a measurement process, a UV process, a heating process, a cleaning process, a preconcentration process, various mixing processes and/or other actions can be stacked against each other for respective subsamples of drawn water; in this manner, the various species can be measured, e.g., to measure masked total selenium, unmakes total selenium, masked Se(IV), unmasked Se(IV), masked Se(VI), unmasked Se(VI), masked organoselenium and unmasked organoselenium, in a manner where processing is both pipelined and highly parallel.

In a second embodiment, the described architecture provides processes that can be applied to multiple different metals in ensuing measurement cycles. For example, the rotary selector technology just described can feature selection ports that support multiple different chemistries, e.g., one for selenium detection and speciation, one for uranium detection and speciation, and so forth (e.g., for other metals or metal species). Following one detection process (e.g., selenium detection and speciation), the various system components are renewed, and an ensuing cycle of preparation steps and measurements are applied relative to the new metal of interest. This optional feature is not required for all embodiments, e.g., as should be apparent, it is possible to have a water metrology system that is geared (or optimized) to analyze only a single metal (and its associated species).

Note that FIG. 2 also depicts various network components that can be used to provide for automated and/or remote measurement and logging. For example, as seen at the lower-right-hand side of the FIG., arrow 235 and a non-transitory storage (database) icon 237 denotes that results can be logged, e.g., to provide historical data, regulatory insight and/or accountability. A cloud icon 239 denotes that control and/or reporting can be performed via a wide area network such as the Internet, for example, with measurement controlled or initiated remotely by a computer system 241, or with results remotely reported, processed and/or logged.

Figure 3:
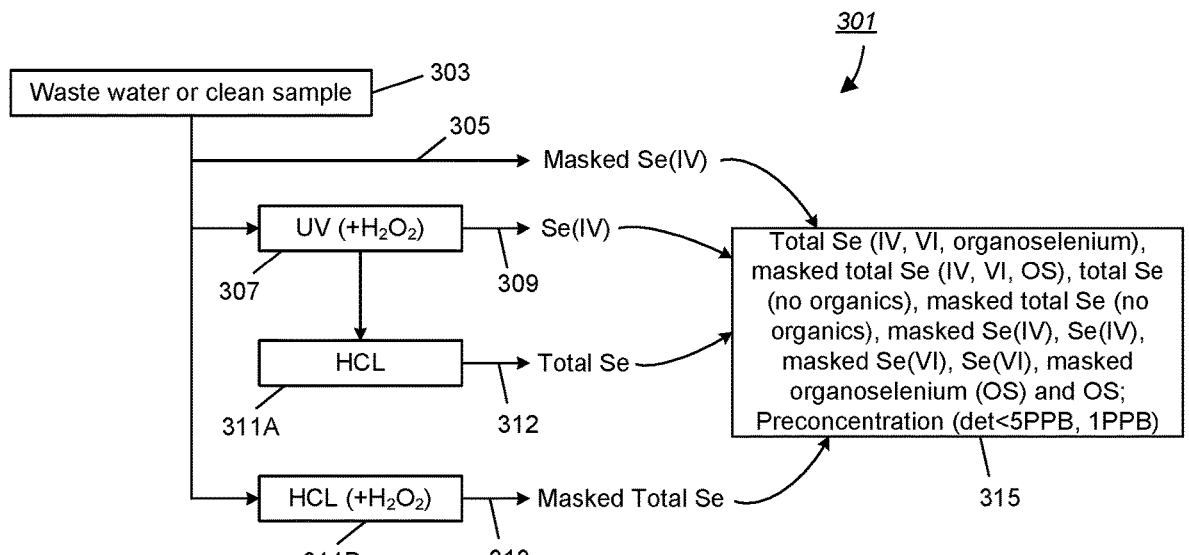
FIG. 3 is a block diagram showing techniques for identifying toxic metal presence in water, notwithstanding the possible presence of organic materials (e.g., polymers) that can mask toxic metal presence.

FIG. 3 is a block diagram that provides additional detail as to how processing can be performed using various subsamples, in this case, rooted specifically in the context of selenium; again, it should be noted that these processes can be applied to other metals as well, and that selenium is used here as an illustrative example.

More specifically, the various processes and actions are collectively denoted by numeral 301. A water sample is first drawn, as referenced by numeral 303; again, this sample can be a "treated" water sample, a "clean" water sample, or a "dirty" water sample, and generally, the sample drawn will be of sufficient size to perform the various species' measurements, e.g., a 50 mL sample. Per numeral 305, a relatively small subsample (e.g., 5 mL) is then withdrawn from the overall sample and sent to the voltametric measurement system, which uses an aqueous copper solution as a catalyst to measure (masked) Se(IV) concentration according to known chemistry. For example, the voltametric system applies a voltage across the mixed solution (i.e. mixed into the measurement cell as described in WO2016174526) and causes Se(IV) to galvanize on a system cathode (or anode), changing measured voltage and/or current in proportion to species concentration. While this process is ongoing, a second 5 mL subsample can be removed from sample 303 and injected into the UV processing component 307 (e.g., with or without hydrogen peroxide) and processed for a 15-minute UV cycle; after this UV treatment is completed, the sample will then be moved to the voltametric system (following renewal and cleaning) to measure unmasked Se(IV), per numeral 309. In addition, some of this UV-processed subsample (or the entire subsample, if desired) can be mixed with an HCl-based reducer and transferred to a heating vessel, per numeral 311A (to mineralize other forms of selenium, converting them to Se(IV)). Per numeral 311B, it is also possible to use a new "dirty" water subsample by removing it from the larger sample 303, mixing it with $H_2O_2$ and HCL, and then heating the subsample. Whichever process is used, and whether or not these processes are used in parallel, the resultant, processed subsamples can then be transferred to the voltametric measurement system (with intervening cleaning and/or rinsing and/or renewal of the mercury electrode, as appropriate). As represented by numeral 315, the various combinations and permutations of these various processes are used to generate respective processed subsamples, which are used to determine total metal presence (e.g., total selenium), masked totals, total selenium (not including organics), Se(IV), Se(VI), organoselenium, masked organoselenium, and potentially other individual species and/or species concentrations. Note that in one embediment, all of this can be accomplished using a measurement system that is only capable of detecting Se(IV) concentration, e.g., by mineralizing and by converting other species forms via the various permutations and combinations referenced above, optionally using both pipeline and parallel measurement processes (i.e., using interleaving of various sample preparation steps and transference steps) as described above. In another variation, as referenced earlier, a preconcentration column can also be used as part of the described processes (e.g., for a "treated" water sample) and used in sequential processes (e.g., that use differential solid phase extraction to isolate Se(IV) and Se(VI), and that use processes to mineralize extracted Se(VI) and deduce Se(VI) concentration from respective measurements of (1) inorganic Se(IV) only, and (2) inorganic Se(IV) together with inorganic Se(VI) that has been mineralized to form inorganic Se(IV)). Other examples will no doubt occur to those having skill in the art.

Figure 4:
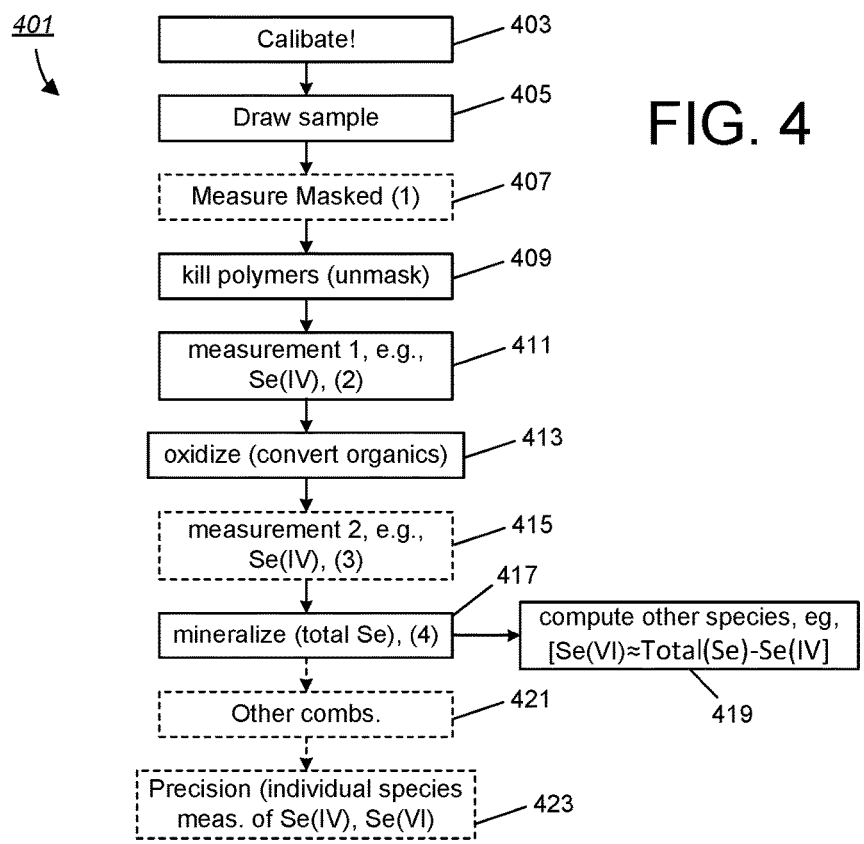
FIG. 4 is a block diagram showing techniques for processing a water sample to identify selenium speciation as part of a single measurement cycle.

FIG. 4 provides another flow diagram 401 that references a set of pipelined processes. As denoted by numeral 403, the system (i.e., the voltametric measurement component or subsystem) is first calibrated, e.g., using a "standard addition" or "spike test" process; for example as additionally described in WO2016174526, a standard (e.g., distilled water with a known, first concentration of Se(IV)) can be added to an already-measured sample and measured to form a second data point, and then an additional standard (e.g., distilled water with a known, second concentration of Se(IV)) can be added to the measurement sample and measured to form a third data point; the resultant measurements permit correlation between a first measurement point (representing raw sample measurement) and a specific concentration of Se(IV) presence, which can be deduced from linear extrapolation of the second and third data points. In a variant, health of the measurement system can periodically be checked (e.g., to detect variation or nonlinearities in this relationship).

Once the system is calibrated, a sample (subsample) can then be drawn (405) and used in an ensuing measurement process (with or without additional processing as necessary). For example, in a first measurement, the raw sample can be measured to detect masked inorganic Se(IV) presence (or a species of another metal) as referenced previously, if not already performed as part of the calibration process (e.g., to yield the first data point). This sample can then be subjected to a UV treatment process to unmask concentration of the (organic and inorganic) metal (409), with a second measurement (411) then being performed to provide relative data (i.e., information on the degree of masking). The UV-processed sample can then be oxidized (413) using a 0.02% to 2% solution of hydrogen peroxide, as referenced earlier, to convert other selenium forms (e.g., Se(0), Se(II-)) to Se(VI), which is then measured by a third measurement process. The oxidized sample can then be mineralized (i.e., using HCL and heating to 90 degrees Centigrade, for 20 minutes, as referenced earlier) to mineralize these other selenium forms, to convert them to Se(IV), per numeral 415, with yet another voltametric measurement (417) performed on this sample. Per numeral 419, software and/or associated circuitry (e.g., a processor) can be then used to compute various metal species based on these measurements. As denoted by numeral 421, various other combinations/permutations of these steps can be performed (e.g., all of the same steps are performed in sequence other than the UV treatment, or with the hydrogen peroxide treatment preceding the UV treatment, and so forth). Per numeral 423, it is also possible to precision-measure "treated" water species using the 0.1M/3.0M HCL sequential column elution processes described earlier and described below in connection with FIG. 9.

FIGS. 5 and 6 provide further block diagrams that are used to describe speciation processes, once again, rooted in the example of inorganic and total Se speciation. The various steps of these block diagrams are respectively identified using numerals 501 and 601.

More specifically, a sample can be applied to a potentiostat detector (e.g. voltametric measurement component) and measured to yield a first metal species, such as Se(IV), as represented by the top most portion of FIG. 5. As indicated by a branch from this first process, a part of that sample can also be fed to a reduction process to convert other inorganic species of the metal of interest (e.g., other inorganic forms of selenium present) to Se(VI), with ensuing measurement then being performed to determine combined inorganic Se(IV) and Se(VI) presence, and to deduce Se(VI) presence relative to the detected Se(IV) presence. As seen at the left-hand side of the FIG., in yet another process, a subsample can also be oxidized (e.g., using $H_2O_2$) and reduced to convert all inorganic forms of selenium (including Se(0) and Se(-II)) to free elements. Concentration of these other inorganic forms can then be derived from differences between measurement of these free elements and the other mentioned measurements.

Per numeral 601, concentrations of organic species can also be deduced from these and additional measurements. As seen in FIG. 6, a UV process is applied to oxidized samples to break down the organics and therefore yield a Se(IV)

concentration representing both organic and inorganic forms, and as well as a Se(VI) concentration representing both organic and inorganic forms. These forms can be mineralized to yield total (organic and inorganic) Se, and from these various measurements, concentrations or organic and inorganic Se(IV) and Se(VI) can be derived, once again, using software operating on a suitable computer/processor.

Figure 7:
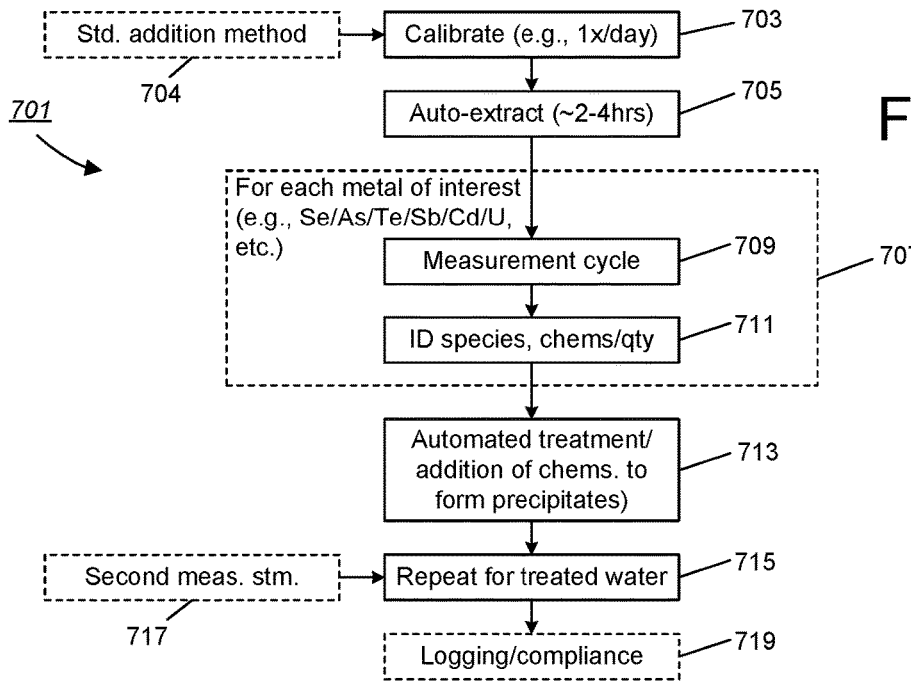
FIG. 7 is a block diagram showing a process for automated measurement of toxic metal presence in water, and actions taken in dependence on identified speciation.
Figure 8A:
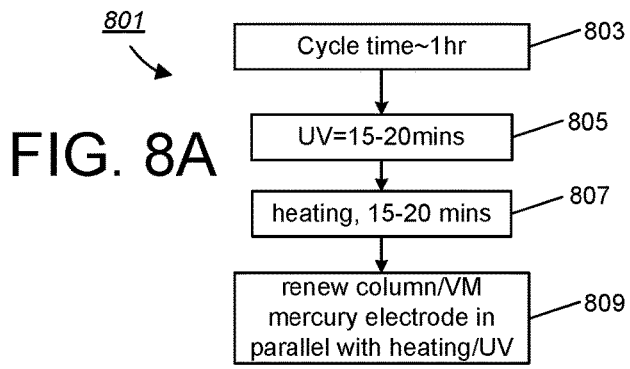
FIG. 8A is another block diagram of a measurement cycle associated with automated measurement of toxic metal presence in water.
Figure 8B:
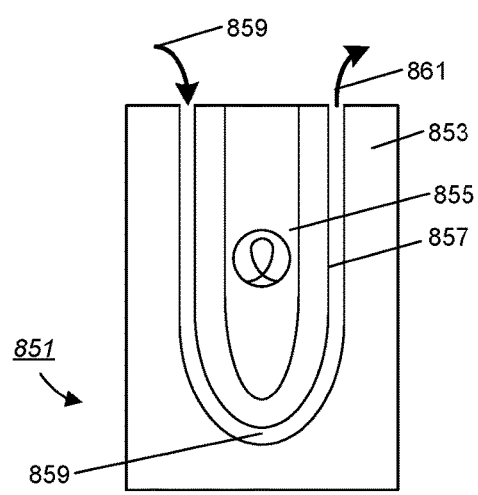
FIG. 8B is a cross-sectional diagram of an ultraviolet light source assembly that can be used to accelerate the measurement cycle of FIG. 8A.

FIGS. 7-8B are used to provide additional detail on techniques for combining these various components and processes to provide for fast, automated, repeated, in-situ analysis of a water supply.

FIG. 7 illustrates a general system process using numeral 701. As indicated, the system is at certain times or intervals (703) calibrated so as to ensure measurement accuracy. This calibration can be remotely controlled and, for example, can be performed once per day (or at a different frequency). As indicated by numeral 704, this calibration is optionally performed using a standard addition method. With system measurement integrity thus ensured, an auto-extraction process is then actuated on an ad hoc basis or according to another desired measurement cycle, for example, each 2-4 hours, or as otherwise desired for the pertinent application (705). A series (707) of measurement cycles (709) are then performed, one for each metal of interest, with measurements performed per cycle as necessary to speciate (711) the particulate metal of interest; for example, a first measurement cycle might be performed for selenium detection and speciation, and a second measurement cycle might be performed for cadmium detection and speciation, with reagents/catalysts/cleaners and other materials been drawn and mixed to samples as pertinent the individual measurement. Once individual metal species as necessary have been detected and measured, control software and/or supporting actuators for the system then provide for automated treatment of/addition of chemicals to the water supply, in precise amounts, so as to precipitate substances that are to be removed from the "dirty" water (713). The water "thus recycled" can then be processed as a "treated" (or "dirty") water supply, for example by repeating the measurements (715) for treated water to reassess presence of them metals of interest; note that in such a system, additional treatment can be automatically performed to further process the water, or an alarm can be triggered if detected metals exceed safe norms. Other actions can also be taken. As represented by numeral 717, in one embodiment, such second measurements are optionally performed by a second measurement system, for example, at a different station in the processing pipeline for treating the waste water. Per numeral 719, all results (or some subset or distillation of them) can optionally be logged and/or reported, for example, for purposes of accountability or providing regulatory compliance.

FIG. 8A shows another block diagram that identifies particulars of a given measurement cycle, generally represented by numeral 801. In particular, as represented by numeral 803, a cycle time for a single metal of interest can take on the order of 1 hour of time, assuming UV treatment 805, heat processes 807 and renewal processes 809 pertinent to the various individual speciation measurements. For one measurement, as described earlier, a sample can be drawn and subjected to UV treatment for 15-20 minutes, then mixed with HCL and $H_2O_2$ (<5 mins), then heated to 90 degrees Centigrade for 15-20 minutes, and then voltametrically measured (<5 mins), followed by an ensuing renewal process that recycles the mercury electrode in the voltametric system for ensuing use (see generally WO2016174526). Careful interleaving of the various processing and measurement steps (and optional use of extra storage vessels, for example, to store one sample while a second sample is being transferred), and parallel processing, are used to help ensure that FIG. 8 represents a maximum cycle time that encompasses the other measurements (i.e., stacked against those measurements). Naturally, for other metals, the cycle time might be longer or shorter depending on the number of species of interest and the number of measurements (and associated processing steps) that have to be performed to detect the pertinent metal species and/or total metal content as appropriate.

FIG. 8B illustrates a UV measurement cell 851 employed in one embodiment to maximize UV absorbance by a sample (subsample of interest). In this regard, the speed with which organics are broken down in a measurement cycle is directly related to the amount of UV energy absorbed by the sample, which in turn is a function of UV intensity, duration, and the efficiency with which UV light is absorbed by the sample. In the depicted example, all elements are housed within a cavity defined within an enclosed aluminum block, which provides for internal reflection of UV light. This is to say, a (250 nm wavelength) UV bulb is represented by numeral 855; this bulb is housed within a hollow quartz sleeve 857 that provides for thermal separation of the UV bulb from the sample being measured. A quartz capillary or concentric jacket provides for fluid circulation outside of the jacket 857 but within the aluminum block 853. As indicated by ingress and egress arrows, 859 and 861, the sample is pumped into this space during UV exposure; light from the UV bulb 855 is directed through the sample and then is continually reflected within the aluminum block to provide for as much efficiency as possible in ensuring that absorption by the sample of UV light; generally speaking, this increase in efficiency shortens a process that might otherwise require exposure time of an hour or more to a 15-20 minute process. The space between the aluminum block and sleeve (e.g., capillary) is sufficient to hold a sample size of approximately 1.5-5.0 m. Once processing is complete, the motion-controlled syringe (or another transport mechanism, such as a Peristatic pump) is then actuated to remove the processed sample for further processing or measurement.

Figure 9:
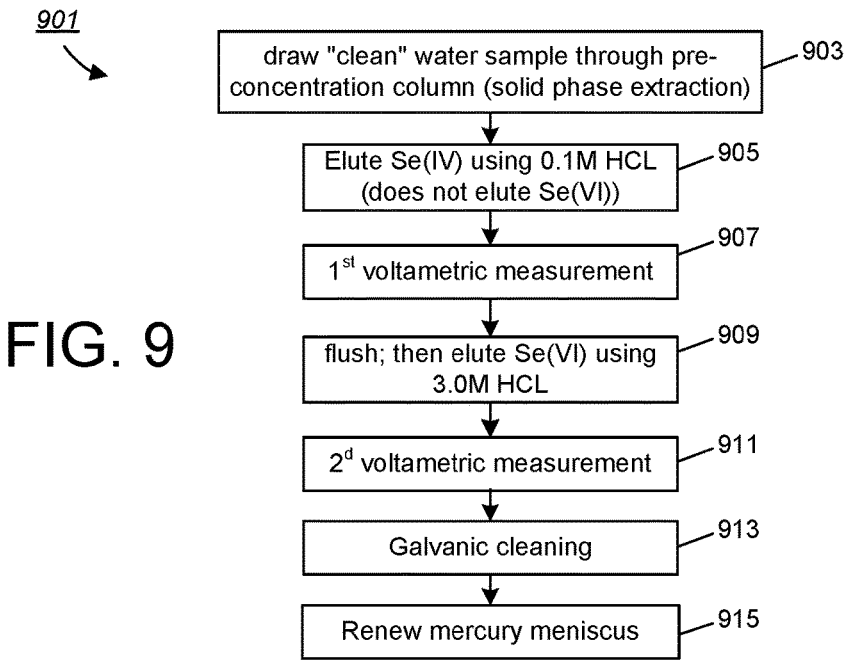
FIG. 9 is a block diagram showing method of operation of a voltametric measurement device for toxic metal speciation in a "treated" water sample.

FIG. 9 provides another block diagram, this time associated with use of the voltametric measurement component for direct speciation. As noted earlier, such a process 901 might not be suitable for a "dirty" water sample (that is, one that might unacceptably degrade a preconcentration column) but, for a clean water sample, metal speciation can be directly performed on a common sample by the voltametric measurement system, depending on metal, species of interest, and the use of suitable chemistry techniques. In the case of selenium, for example, a voltametric technique using a copper catalyst can measure selenium present, with differential elution from the concentration column used to differentiate Se(IV) and Se(VI) species. That is, as represented by the FIG., per numeral 903, a "treated" 5.0 ml water sample is first driven through a preconcentration column or extraction media (e.g., as further discussed in WO2016174526); this process can be used to elute or extract inorganic Se(IV) and Se(VI), and potentially other species of this metal, in effect, transferring them from the water to the elution media. With solid-phase extraction thus effectuated, a small amount (e.g., 1 ml) of 0.1M HCl is then passed through the extraction medium, per numeral 905. This weak acid is sufficient to elute Se(IV) but not Se(VI) which remains in the column (if desired, a liquid-to-liquid exchange process can be used to transfer eluted selenium to another solution). Per numeral 907, a first voltametric measurement is then performed to precisely detect Se(IV) concentration in the solution. Per numeral 909, the system is then flushed (e.g., with distilled water and/or a cleaner) and the process is then repeated, this time, however, using 3.0M HCL, which is sufficient to elute all remaining selenium from the preconcentration column (i.e., Se(VI)); once again, if desired, a liquid-to-liquid exchange process can be used to transfer the eluted selenium to another carrier. After the reduction of Se(VI) to Se(IV) a second voltametric measurement is then performed to precisely measure Se(VI) concentration (911). The system is then galvanically cleaned (913), i.e., to remove contaminants from the mercury, and the meniscus of the mercury electrode is then renewed (915) to prepare its use for an ensuing measurement. The process represented by FIG. 9 represents an efficient mechanism, provided by the structures described herein, for directly measuring speciation in a "treated" water sample, that is, when the sample to be measured is of a nature where soluble organics (or other particulate) will not degrade the extraction column. Using preconcentration (i.e., where ions can be extracted from a water sample and concentrated in a relatively smaller volume of a solution used to elute the ions of interest), it believed that the describe system can identify concentrations at levels equal to or less than approximately 1 part per billion (i.e., 1 ppb).

Figure 10:
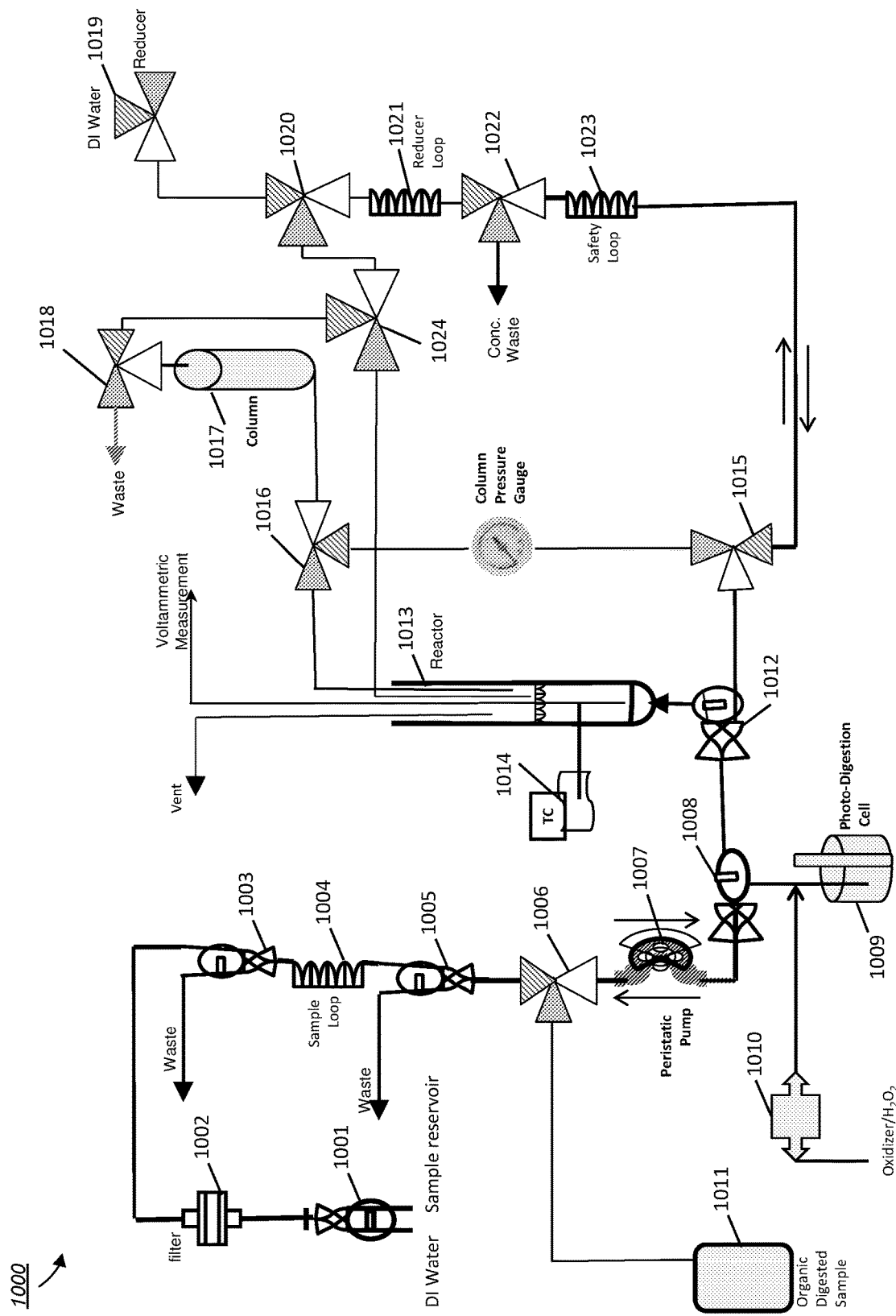
FIG. 10 is a schematic diagram of a system for automated measurement of toxic metal presence in water.

FIG. 10 provides a schematic diagram showing another embodiment 1000 of a system for performing various extraction, transport, processing and measurement as described herein. More specifically, it is to be assumed for this example that a sample with high organic content is to be first photo-digested and then oxidized in order to mineralize a metal type which is present. A sample with less organics can be directly mineralized and measured for speciation, for example, being concentrated on solid state column to lower the detection limit of voltammetric instrument. The sample is pulled from sample reservoir by a peristatic pump 1007 through valves 1001, 1003, 1005, 1006 and filter 1002. The loop 1004 is filled, and excess sample is pushed to waste through a valve 1005. A precise volume of sample is then pulled from sample loop through valve 1005 and pushed to photo-digestion cell 1009 via valve 1008, to reactor 1013 via valves 1008 and 1012, or to the solid state extraction column 1017 via valves 1008, 1012, 1015 and 1016. For photo-digestion of sample with high organics, a small amount of hydrogen peroxide ($H_2O_2$, e.g., 1 to 100 ppm), is added via diaphragm pump 1010 and the sample subjected to UV-lamp radiation for predetermined time ranging from 15 minutes to 2 hours (depending on factors such as UV lamp power, configuration of the irradiation system, sample size, and other factors). After digestion, the irradiated sample is then divided into two parts; one part is pushed into reactor 1013 for the metals that required mineralization. For mineralization a precise amount of reducer is injected to reactor 1013, pulled through valves 1019, 1020, 1022 and 1015 by pump 1007, and then pushed through valve 1024. Solution in the reactor is heated to a pre-determined temperature (controlled using a thermostat 1014). A second portion of digested sample from the photo-digestion cell 1009 is pulled by pump 1007 and pushed through valves 1008 and 1006 into reservoir 1011. This digested sample is used to measure metals that do not require (or where the sample is not amenable to) mineralization or concentration.

Figure 11:
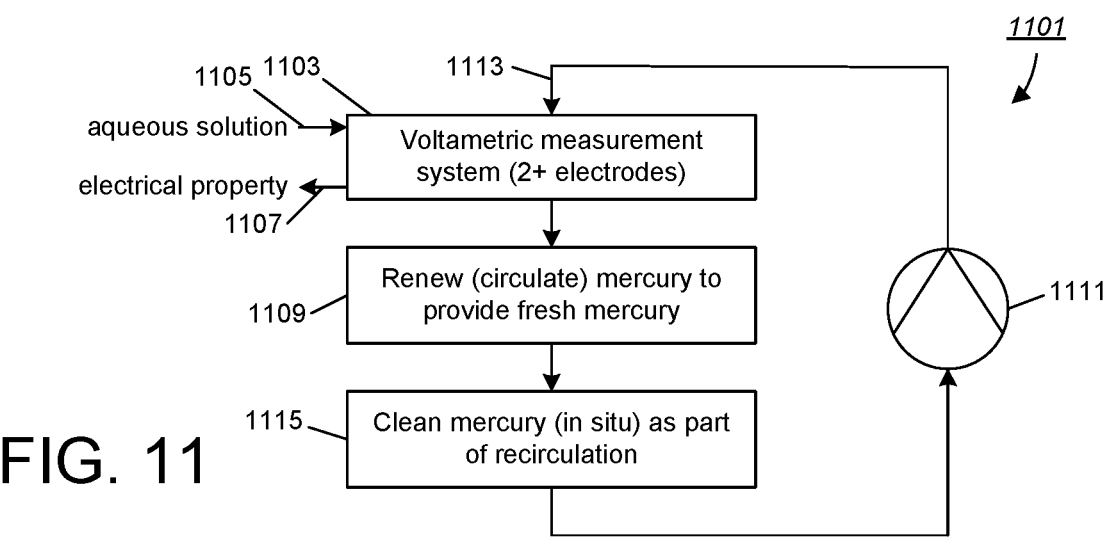
FIG. 11 is a block diagram showing a voltametric measurement system with a renewable mercury electrode.
Figure 12:
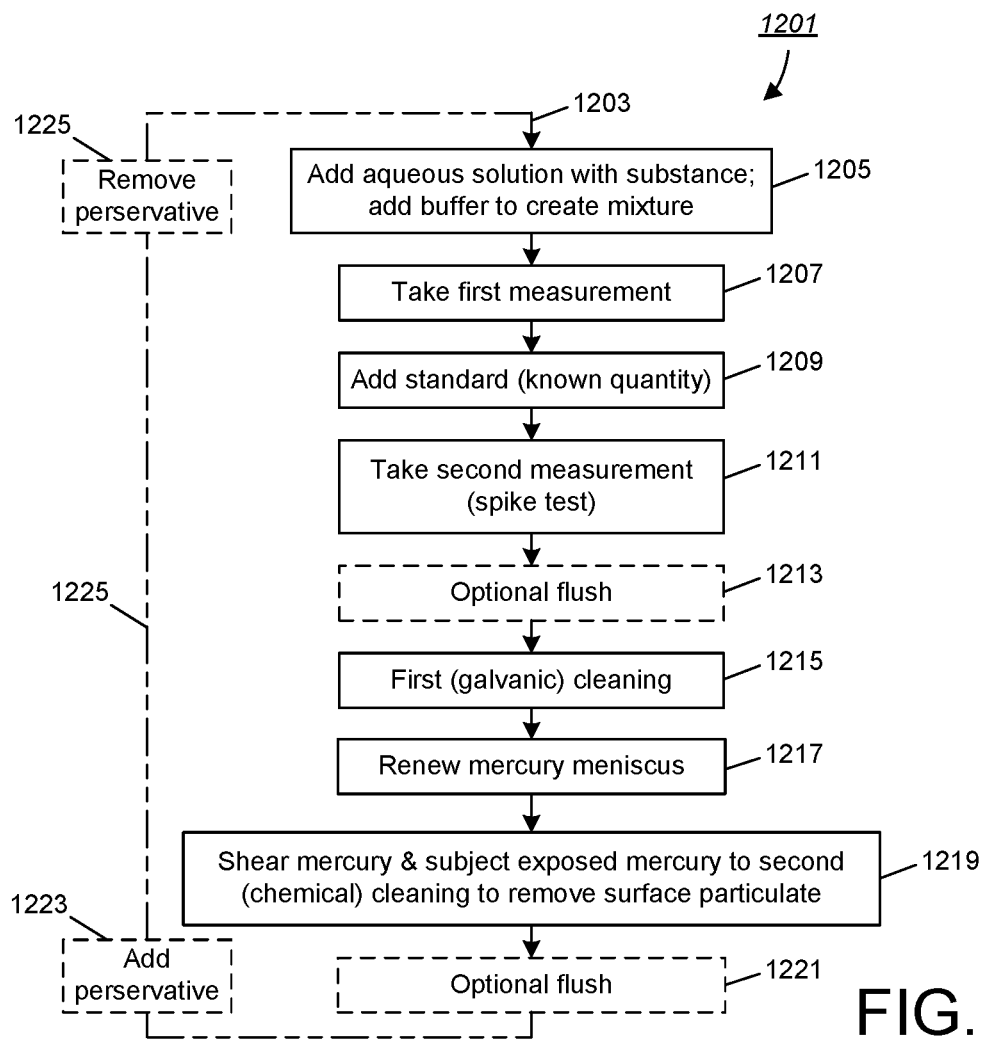
FIG. 12 is a block diagram showing calibration of the voltametric measurement system of FIG. 11, i.e., based on a "standard addition" or "spike test" method.

FIGS. 11-12 provide more detail on an exemplary voltametric measurement device. While many different types of systems are known, in one embodiment, the measurement device is predicated on the use of liquid mercury as an electrode surface ("mercury meniscus electrode" or "mercury electrode"). This design uses a mercury recirculatory system that provides for very low overall liquid mercury volume, and for reclamation, in-situ cleaning and renewal/recycling of the liquid mercury. This fosters a mercury supply that can be used repeatedly over a long lifetime, that is, without excessive mercury waste and without exposing an operator to mercury or other harmful chemicals; in designs presented below, overall system volume of mercury can be to kept less than two-hundred fifty microliters and, in some embodiments, less than a hundred or even fifty microliters (μl). This disclosed structure facilitates unlimited or nearly-unlimited reuse of the liquid mercury with virtually no waste mercury, and thus helps address potential health and ecological hazards; it also provides for a potentially less expensive and more reliable electrode and related system operation. Techniques for enabling these ends will be discussed below.

Conventional voltametric measurement systems use either two or three electrodes to measure an electrochemical property of an aqueous solution (generally current), to deduce presence and concentration of a material (i.e., an analyte of interest, such as selenium, in keeping with the earlier examples). Many different electrode materials can be used depending on desired application. To perform measurement, the electrodes are immersed in an aqueous solution to which a buffer has been added to provide for chemistry tailored to the detection of the specific analyte. Application of controlled potential difference is usually provided by a potentiostat, with change in the desired electrochemical property being measured as the potential difference is varied. As noted earlier, some systems utilize liquid mercury as an electrode (i.e., as a generally hemispherical mercury meniscus), because, in part, mercury is chemically inert, because conductivity is excellent and provides for ultra-low detection limits, because the liquid mercury provides high hydrogen evolution overvoltage (i.e., a broad potential window) and provides for ultra-low detection limits, and because the surface tension of liquid mercury allows for a highly-repeatable surface structure (and thus highly repeatable electrode surface area). These features permit mercury to be used to measure trace quantities (e.g., parts-per-million or parts-per-billion) of many analytes.

Because repeated measurement can corrupt a working electrode and can create precipitate or other particulate as adsorption layers, conventional systems predicated on a solid (i.e., non-mercury) electrode often require extensive manual cleaning procedures (e.g., scrubbing or ultrasonic) before a measurement can again be performed. For liquid mercury electrodes, abrasive cleaning is often not practical due to instability of the liquid mercury, with the result that mercury is often treated as a consumable.

To address this, in one embodiment, the measurement system described earlier uses mercury as a renewable resource, that is, where liquid mercury is not disposed of, but rather is cleaned and reused, and in a manner where human-mercury interaction is minimized. The design of such a voltametric measurement system and its method of operation is generally described in WO2016174526 (i.e., the patent publication which has already been incorporated by reference). A number of design techniques contribute to these ends, depending on embodiment. Generally, speaking, a measurement system comprises two or more electrodes, one of which is a mercury electrode (e.g., dropping mercury electrode, hanging mercury electrode, mercury meniscus electrode or other electrode that relies on liquid mercury), and a system for recirculating and/or recycling mercury. As measurements occur, a pump is used to renew a mercury meniscus at a tip of the mercury electrode, expelling a quantity of "used" mercury from a tip of the electrode under the force of pressurized mercury, and providing for a new mercury meniscus for use in an ensuing measurement. Used mercury shed or sheared from the electrode tip is then gravitationally collected by a trap, and is provided to the pump for eventual resupply to the mercury electrode to provide a future, renewed liquid mercury surface. At some point in this mercury loop, an in-situ cleaning mechanism is used to clean contaminants from the liquid mercury, and to thus provide used, recycled mercury without the need for mercury disposal. This cleaning can be performed on liquid mercury at any point in the system, with a number of specific cleaning mechanisms being exemplified below. As should be apparent, this design provides for substantially reduced mercury waste and for a degree of automation heretofore unexperienced. Because liquid mercury can be cleaned in-situ, e.g., using automated mechanisms, a voltametric system based on a mercury electrode can be fully automated and used for remote (or repeated) measurements, with a high degree of reliability and with a lifecycle of hundreds or thousands of measurements, or more, before serving is required. Such a design contributes to the automation and remote-use capabilities of the overall measurement system, as referenced earlier, and facilitates a design with minimized required maintenance.

FIG. 11 shows an embodiment of the voltametric measurement component or subsystem, generally referenced by numeral 1101. A voltametric subsystem predicated on the use of two or more electrodes 1103 receives an aqueous solution 1105 (e.g., a "dirty" or "treated" water sample drawn from a supply) that is to be measured to detect a parameter associated with a desired analyte, in this case, toxic metal presence. As indicated by numeral 1107, the voltametric subsystem typically measures an electrochemical property that will be processed to determine whether the desired analyte is present, and/or the concentration of such an analyte. In the example referenced above, a voltametric subsystem can be used for waste water processing, to detect presence and concentration of individual toxic metal species (i.e., metals such as arsenic, lead, copper, chromium, beryllium, cadmium, aluminum, nickel, uranium, selenium, zinc and so forth). As indicated by numeral 1109, one of the electrodes (typically the working or main electrode) is a mercury electrode that provides a liquid mercury surface that will be in contact with the aqueous solution for the purpose of providing current flow and associated electrochemical measurement; a mercury recirculatory system, for example, including a pump 1111 and mercury loop or path 1113, is used to collect used or spent liquid mercury shed from the working electrode and to recycle that liquid mercury for renewed use. That is, for example, after the aqueous solution has been measured, it is not thrown out together with spent mercury, but rather, liquid mercury is harvested from the aqueous solution and is recycled. Cleaning 1115 can occur at any point in the mercury loop (i.e., at any point along the liquid mercury flow path, whether as part of the measurement mixture or solution, as part of the electrode, or otherwise in the recirculatory path).

FIG. 12 provides additional detail on a more specific implementation where liquid mercury is reused and where control over a measurement system is to be at least partially automated. Such a subsystem is generally designated by numeral 1201. More specifically, functional block 1203 indicates that an aqueous sample of specific volume is received for measurement. Note that an aqueous solution can be prepared or obtained in many different ways, for example, either natively received as a substance that is directly to be measured (e.g., waste water or another type of liquid) or otherwise received in a first form (e.g., clean water) with a specific substance (e.g., selenium species) eluted to or transferred to an exchange medium or column as part of a sample preparation step. Whichever preparation methodology is used, as indicated by numeral 1205, a buffer or catalyst is then added to the aqueous solution to select the specific chemistry that will be the subject of measurement (e.g., charge transport provided by a particular analyte) and to produce a mixture. In the case of selenium, an aqueous copper solution can be used. Note that in some embodiments, a mixing step can also be employed to ensure measurement of a homogeneous mixture, and in other embodiments, the mixture can be heated, chilled, or otherwise processed or allowed to react to any desired degree prior to measurement, as suitable to the selected chemistry. In a typical application such as a water metrology application, the buffer solution can be added to emphasize a particular material (e.g., a specific metal) that is to be measured, to facilitate ionic or other charge transport involving the desired analyte under the influence of a potential difference. This measurement is effected by a first voltametric measurement taken of an electrochemical property of the aqueous solution and of mixture (i.e., generally current flow).

In a laboratory setting, a measurement system might be the subject of frequent system calibration (i.e., of electrode sensitivity), such that when a substance of interest is later measured (e.g., as this first measurement), the measured electrochemical property can immediately be processed using stored calibration results to directly yield analyte concentration. In the depicted embodiment, as introduced earlier, such an advance process is not used; rather, in order to facilitate repeated, automated measurements of a particular substance of interest (e.g., selenium concentration in a waste water supply), a "standard addition" or "spike test" is performed (1211), in which the first measurement just referred to is then supplemented with one or more additional measurements following the addition of a known standard of specific volume to the mixture (1209). As the addition of the standard will change measurement results, and as the relationship between analyte presence in the standard and the measured electrochemical property for the standard is known, the concentration of analyte in the aqueous solution can be determined dependent on the results of the additional measurements for the electrochemical property and the relative volume of the aqueous solution and of each added standard. In one embodiment, only one such spike test is performed, while in another embodiment, multiple spike tests are performed and used to assess linearity of the results (i.e., for diagnostic or other purposes). Once the desired number of measurements is performed, cleaning is then performed, per numerals 1215 and 1219, mercury gravitationally settles out of the solution and is collected and the solution is discarded. Optionally, as indicated by numerals 1213 and 1221, the system can be flushed or rinsed before or after such cleaning. Note that because mercury is harvested, there is little to no dissolved mercury in the discarded solution. This differs markedly from some conventional systems where grams of mercury metal can be a waste product of each measurement iteration; the present technology permits mercury to be recycled on an indefinite or nearly indefinite basis with little to no mercury replacement or servicing needed, depending on implementation.

Note also that, as indicated in FIG. 12, in the depicted embodiment, two different in-situ cleaning operations are performed; per numeral 1215 a first, galvanic cleaning is performed (i.e., in which the voltametric subsystem is caused to reverse the potential difference between electrodes, to draw mercury amalgam (metals dissolved in mercury) back into the ionic species in the aqueous solution), and a second cleaning (1219) is performed to remove precipitates (e.g., solids, adsorbed matter) from surfaces within the measurement system (including one or more liquid mercury surfaces). In various embodiments, one, two, or indeed any number of in-situ cleaning operations can be performed; this embodiment illustrates two specific cleaning processes.

As to the first of these depicted cleaning processes, as noted earlier, absorbance of metal species can form amalgam, which is not desired. Therefore, for galvanic cleaning, the reversing of electrode potential draws spurious metals in the opposite direction, out of the liquid mercury, such that if analyte metal ions were attracted to mercury during measurement, the potential difference is used to draw those ions back out of the mercury bulk, and thus help clean the liquid mercury and reverse amalgam formation. In this regard, in a two or three electrode system, platinum is advantageously used as the auxiliary electrode and as a galvanic wire for use in such a process; platinum is relatively inert and stable, chemically speaking. Other metals or conductive materials can also be used where those materials are sufficiently inert and stable relative to the chemistries to be used in measurement. Note that the amount of potential difference, and time for which this difference is to be applied, can be determined by one of ordinary skill in the art, as suitable to the particular chemistries. Also, while FIG. 12 illustrates a galvanic cleaning process as a constituent part of the depicted measurement cycle (i.e., it is performed immediately following measurement, to avoid fast diffusion of the amalgam into the mercury bulk, for each-and-every measurement cycle), in other embodiments, this need not be the case (e.g., cleaning can be performed as part of a specific cleaning cycle, on an ad hoc basis once a detected level of degradation has been reached, once every few measurement cycles, or at the start of each day, or on another desired basis). In part to ensure measurement-to-measurement results consistency and to maintain the liquid mercury in as virgin a state as possible, in one contemplated embodiment, galvanic cleaning is performed following each-and-every measurement (i.e., each voltametric scan). Note also that because galvanic cleaning utilizes a reversal in voltage polarity, it is most effective for the liquid mercury that is still at the tip of the mercury electrode, i.e., this type of cleaning is typically performed prior to the shedding of spent or used mercury and renewal of the mercury meniscus for a subsequent measurement cycle.

As to the second depicted cleaning process, it is noted that many solutions will feature multiple contaminants, only one of which is the subject of a given measurement, and that contaminants can take a variety of forms including precipitates that might build up over time and contribute to measurement noise (and thus raise detection limits for ensuing measurements). For example, some metals (such as selenium) or other organic or inorganic materials can create sediments that, absent special measures, would build up over time. As will be discussed further below, in the depicted embodiment, a number of features combine to provide for an effectively chemical cleaning of such sediments in between the measurement of respective solutions. First, in one embodiment, a cleaning solution is added following use of a particular aqueous solution to strip or otherwise dissolve surface particulate; such a solution can take the form of a chelating agent, an acid, a base, a reagent, deionized water, or another material that dissolves or otherwise removes surface contamination of interest from the measurement cell and from the surface of collected liquid mercury. The optimal cleaning agent will vary according to the measurement chemistry, and its selection is well within the abilities of a skilled chemist. The cleaner is advantageously chosen so as to not be harmful or noxious given assumed human contact, and so as to not require special disposal procedures. For example, in a case where nitric acid is used (given the particular measurement chemistry), the cleaner is typically chosen to have relatively low acid concentration (e.g., 0.1M) yet to provide for a relatively low pH and satisfactory stripping performance.

In some embodiments, measurement occurs in a measurement cell where spent or used mercury is shed, falls gravitationally through the cell and through the solution, and collects and coalesces in a mercury trap; by providing for a relatively small area where spent mercury is collected and channeled, and thus a concentrated surface for a pool of collected liquid mercury, and by adding the cleaning agent in proximity to this surface (i.e., where contaminates precipitate or are otherwise concentrated), contaminant removal is facilitated. In one embodiment discussed further below, a special measurement cell is disclosed which permits liquid mercury to be pooled in a trap or column (e.g., less than 5.0 mm in diameter) with localized cleaning solution injection for this purpose (see generally WO2016174526). Because sediments can build up over time, and ultimately could potentially work their way in to the mercury recirculatory system to denigrate electrode performance, this cleaning step is also performed for each measurement cycle, but after the spent mercury is shed from the electrode (1217).

While two cleaning processes have been disclosed which remove contaminants that might otherwise interfere with the performance provided by the liquid mercury, in fact, there are many more cleaning processes that can be electively applied in-situ, in addition to or in lieu of those just mentioned. For example, another in-situ cleaning process involves backflushing the mercury recirculation system to draw cleaning solution into the mercury electrode (i.e., into the channel used to supply liquid mercury to the electrode tip) and pump this solution into through the pump and into the mercury trap; such a process can potentially remedy blockage issues in the mercury recirculatory system, as well as remove contaminants from inside the recirculatory system (e.g., in the pump or tubing used to transport liquid mercury). Other in-situ cleaning processes will also occur to those having skill in the art.

Also, note that in some embodiments, various forms of sensors or measurements (e.g., voltametric measurements) can be used to verify proper system operation and to take remedial measures to improve performance. For example, the linearity test referenced above (and/or other tests, such as an electrical continuity test), if performed and determined to produce a threshold amount of error, can be used to trigger mercury backflushing as just discussed. Alternatively, an image sensor (e.g., a camera or other sensor) can be used to measure mercury properties (e.g., purity, volume and so forth) and alert an operator if a problem exists.

Finally, as noted per numeral 1221, once cleaning has been completed, the measurement cell can then be flushed (e.g., with cleaner or deionized water, if the cell has not be rinsed already). Note that with a system having a mercury electrode, a typical auxiliary electrode structure (platinum) and a reference electrode, if any (e.g., an insulated silver/silver chloride electrode), the humidity provided even following draining of the measurement cell is typically sufficient for electrode preservation in between measurements. In an automated measurement system, if measurements are only to be performed very infrequently (e.g., once per day or less frequently), the measurement cell (or area) can optionally be filled with a preservative (e.g., such as a cleaner or deionized water) so as to preserve electrode health, as indicated by numerals 1223 and 1227. Per numeral 1225, the measurement system can then be reused for new measurements as desired, as part of a new measurement cycle.

As should be apparent, FIG. 12 provides for a method for automated measurement system that relies on voltametric techniques. The represented process can be automated in the sense that, whether by command or otherwise, a series of sequential steps are performed "automatically," under the governance of an electronic control system, after a sample has been received; the steps are performed in a sequence without requiring manual intervention and typically include mercury cleaning and mercury electrode renewal. Optionally, such an automatic cycle can be performed on demand (e.g., any time a command from a human operator), in response to detection of another ad hoc "trigger" (such as detection of a particular, monitored condition) or on an automated, calendared basis (for example, "every 2 hours"), as has previously been introduced. When employed in combination with pipelined sample processing of the type described earlier, and when implemented on a basis where each subsample processed by the system is milliliter scale, it should be apparent that the various designs described herein provide for automated measurement with little consumable or waste.

It should be appreciated that a number of elements (e.g., the rotary selector, motion-controlled syringe, a reaction vessel and so forth) can be overlapped with the waste water measurement system described earlier, with measurement cell and associated mixing and other substructure mixed and matched with the components described above. Additional modifications and substitutions will also no doubt occur to those having skill in the art.

As can be seen from this discussion, embodiments presented herein provide a novel, automated way to calculate each individual species of interest. These mechanisms also provide for cooperation among multiple entities, each of which can optionally practice a "piece" of the techniques described earlier (i.e., such that one entity uses software that permits it to interact with software or systems optionally used by another entity). This includes various control processes which can be aggregated at a central location or distributed, depending upon embodiment. As alluded to earlier, a control system may, as part of an in-situ device, part of a local area network ("LAN") or over a wide area network ("WAN," e.g., the internet), automatically monitor a substance of interest and take remedial action, for example, by sounding or otherwise triggering an alarm, or by using an electronic control system and the feedback provided by periodic measurements. In one contemplated embodiment, these techniques can be applied to a waste water monitoring system; for example, with such an automated measurement mechanism, it becomes possible to immediately adjust chemical treatment upstream in a water supply dependent on automated, downstream monitoring. Such a system may be run continuously, 24 hours per day, unattended, with a warning indication or other action if contaminants exceed a specified limit, responsive to a detected maintenance condition, or on another ad hoc basis.

Figure 13:
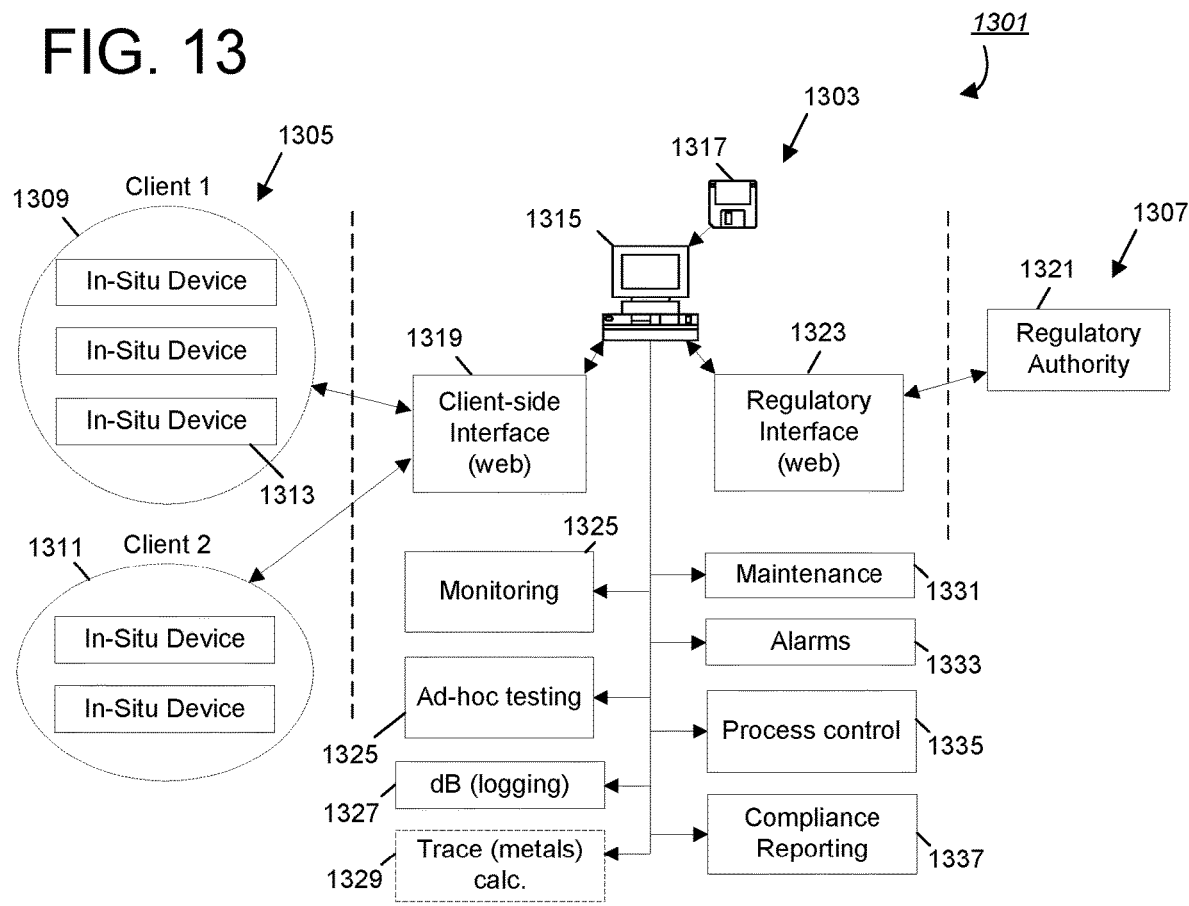
FIG. 13 is a block diagram showing automated, remote use of a measurement system in association with a water supply, and associated network processes.

FIG. 13 provides a system diagram 1301 used to explain a method of remotely monitoring one or more in-situ mechanisms or devices. Once again, measurement of a waste water supply is used as an application example, but the disclosed techniques can be applied to measurement of any other substance, whether or not fully automated, and whether or not such involves water metrology. More particularly, FIG. 13 is seen to be divided into middle, left and right portions (1303, 1305 and 1307) that respectively represent (a) an on-line or other business that for a fee may automatically monitor a substance (e.g., one or more water supplies), (b) one or more clients of the business (e.g., one or more municipal water companies), and (c) a regulatory authority or other entity that is to monitor results or receive reporting of compliance. FIG. 13 illustrates two hypothetical clients 1309 and 1311, each of which may be taken for this example to be a water company, and each of which may have one or more in-situ devices 1313 for monitoring a particular portion of a water delivery network (only one in-situ device is numerically labeled to simplify the illustration). In this regard, it should be assumed that the method (e.g., the business) is to automatically and/or remotely collect measurement data for the purposes for compliance reporting or other purposes; to this effect, the business 1303 includes a supervisory control mechanism 1315, depicted as one or more computers running software 1317 (e.g., a server system), with this system interfacing both with each client (via a client-side web interface 1319), and with a regulatory authority 1321 (via a regulatory side interface 1323). In one embodiment, the regulatory side web interface may provide a portal for regulatory authorities to remotely audit current and past individual operations (e.g., water supply operations), with further ad hoc tests being initiated as required, and with the business interacting with regulatory authorities on behalf of each client, if desired or appropriate, in a manner transparent to each client. Each interface 1319/1323 may permit different access levels and present different authentication requirements (e.g., a specific type or level of PKI authentication). For example, because the client side interface may be used for automated communication with each in-situ device 1313, each such device may be made to have an embedded cryptographic key for purposes of authentication; on the other hand, because regulatory interaction may involve aggregated, relatively sensitive data, or for other security reasons, two-factor or other authentication requirements may be used as a predicate for individual access by a remote human user. Regardless of the interface formats, the supervisory system can be configured to perform a number of functions, depicted at the middle of FIG. 13, thereby relieving the clients 1309 and 1311 from the need to perform these functions themselves, and minimizing the need for on-site presence or inspection by regulatory authorities. As indicated by reference numeral 1325, the method may include periodically receiving test data from each one of the plural in-situ devices 1313 via the client-side interface 1319; each instance of test data may represent an automated process that is initiated by the specific device 1313, and/or the supervisory system 1315 may also selectively initiate tests. For example, if it is determined that a specific metal ion as determined from a test is out of normal bounds, an ad hoc test may be commanded by the supervisory control system, as indicated by reference numeral 1325. The supervisory control system may perform data base management (1327), indexing each set of test data by particular provider, time and date, last known calibration, and any other desired data. As indicated by blocks 1331, 1333, 1335 and 1337, the supervisory control system (or a different electronic control system) may also test for and/or respond to maintenance events, generate alarms or take process control actions responsive to comparison of trace levels of various toxic metals or other specific substances against thresholds, and generate automatic compliance reports either for the regulatory authority 1321 or a particular client 1309 or 1311. As further depicted by a dashed-line, optional block 1329, if desired, raw data may be reported to the supervisory control system 1315, with total and/or individual metal species calculations being performed by the supervisory control system 1315, on a remote basis.

Reflecting on the principles discussed, what has been described are systems, methods, devices, designs and techniques for providing toxic metal detection and speciation useful in analyzing "dirty" water supplies, i.e., waste water having organic compounds that might foul conventional measurement systems predicated on the use of an extraction media or mass spectrometry. The described systems provide for automated, remote, field use, and provide for far more accurate results than would be obtainable using conventional field-based methods and equipment. Further, these systems facilitate safer treatment of a water supply, both minimizing treatment chemicals that must be used and reducing that toxic substances might be "missed" in distributing recycled water. The disclosed techniques can also be applied to "treated" and/or "clean" water samples, as well as to measuring multiple different metals. As should be apparent, therefore, the present disclosure provides for substantial advances, not only in the measurement process, but also in terms of compliance and accountability, potentially changing the way in which water companies and regulatory authorities conduct business.

Applying the techniques described above, in one embodiment, an in-situ measurement mechanism draws samples from a water supply on an intermittent basis (e.g., periodically, on command, or at the occurrence of certain events). The in-situ measurement mechanism is configured to detect concentration of a specific metal species, wherein there may be other different species of the same metal present or substances that interfere with measurement (e.g., organics). The in-situ measurement mechanism processes a subsample, for example, using a chemical, heat, UV, or other process to change the different species of the same metal (or the other substances present, such as unwanted organics or inorganics); for example, in one embodiment, this processing converts one or more of the "other metal species" to the specific metal species that the in-situ measurement mechanism is configured to measure, and in another embodiment, this processing destroys, converts or removes the other substances, for example, breaking down organics such as polymers. If desired, automated filtration can be performed at any step of the process. Differential measurements of the specific metal species are then taken, e.g., one with the processing having been applied and one without, permitting measurement of the specific metal species both with and without processing (in one embodiment), and permitting differentiation between the specific metal species present in tested water and other metal species which have been converted to the specific species. Other measurements can be taken and used in combination with the various techniques above, and various automated reactive measures can be taken in response to the described measurements; for example, treatment chemicals and quantities of treatment chemicals can be selected, adjusted, and automatically used to treat water, thereby avoiding chemical over-usage while safeguarding the environment and human health.

Various alternatives to the foregoing techniques will readily occur to those having skill in the art. To pick just a few examples, techniques mentioned above may be applied using other types of applications, chemistries, analytes or processes. Many other variations also exist. Accordingly, the foregoing discussion is intended to be illustrative only; other designs, uses, alternatives, modifications and improvements will also occur to those having skill in the art which are nonetheless within the spirit and scope of the present disclosure, which is limited and defined only by the following claims and equivalents thereto.

We claim:

1. An apparatus for the measurement of metal concentration in an aqueous matrix, the apparatus comprising:
   an extraction mechanism to draw samples of the aqueous matrix from a supply;
   a measurement device to measure concentration of a specific chemical specie of a predetermined metal;
   a subsystem to process at least one of the samples using predetermined processing, the predetermined processing including at least one of chemical processing, heat processing or ultraviolet light exposure, to create one or more processed samples;
   a transfer mechanism to transfer samples to the measurement device for measurement of the concentration of the specific chemical specie of the predetermined metal, including at least one of the one or more processed samples, and a sample drawn from the supply which has not been subjected to the predetermined processing; and
   a control system;
   wherein the predetermined processing further comprises at least one of removal of an organic material from one of the samples drawn from the supply, or conversion of a different specie of the predetermined metal present in the one of the samples drawn from the supply to the specific chemical specie; and
   wherein the control mechanism is to control the extraction mechanism, the measurement device, the processing subsystem and the transfer mechanism on an sequential, automated basis, to obtain at least two measurements of the concentration of the specific chemical specie including measurements with and without the predetermined processing respectively.

2. The apparatus of claim 1, wherein the predetermined metal is selenium and wherein the specific chemical specie comprises Se(IV).

3. The apparatus of claim 2, wherein the measurement device comprises a voltametric system with a renewable mercury electrode and a cleaning mode in which the voltametric system is to extract amalgam from the renewable mercury electrode.

4. The apparatus of claim 2, wherein the different specie comprises Se(VI).

5. The apparatus of claim 1, wherein the predetermined metal comprises an element from the group of alkali metals, transition metals, non-metals, metalloids and rare earth elements.

6. The apparatus of claim 1, wherein the predetermined metal comprises an element from the group of selenium, cadmium, lead, copper, arsenic, chromium, beryllium, aluminum, nickel, uranium, selenium, and zinc.

7. The apparatus of claim 1, wherein the control system is to compute a value representing selection of a treatment chemical to be applied to liquid corresponding to the samples in order to treat the supply, the value dependent on a measurement of the at least two measurements, and to output a result representing the value.

8. The apparatus of claim 1, wherein the control system is to compute a value representing selection of a quantity of a treatment chemical to be applied to liquid corresponding to the samples drawn from the supply in order to treat the supply, the value dependent on a measurement of the at least two measurements, and to output a result representing the value.

9. The apparatus of claim 1, wherein the predetermined metal is selenium, wherein the predetermined processing is to process organoselenium from one of the samples drawn from the supply to convert the organoselenium to an inorganic form, and to convert the inorganic form to Se(IV) for one of the samples drawn from the supply.

10. The apparatus of claim 1, wherein the predetermined processing is to heat one of the samples drawn from the supply and to introduce an acid to the one of the samples drawn from the supply to mineralize one or more species of the predetermined metal.

11. The apparatus of claim 1, wherein the aqueous matrix comprises waste water.

12. A method of measuring metal concentration in an aqueous matrix, the method comprising:
   using an extraction mechanism to draw samples of the aqueous matrix from the supply;
   measure concentration of a specific chemical specie of a predetermined metal with a measurement device;
   applying predetermined processing to at least one of the samples using a processing subsystem, the predetermined processing including at least one of chemical processing, heat processing or ultraviolet light exposure, to create one or more processed samples;
   transferring samples to the measurement device for measurement of the concentration of the specific chemical specie of the predetermined metal using a transfer mechanism, the transferred samples including at least one of the one or more processed samples, and a sample drawn from the supply which has not been subjected to the predetermined processing; and
   wherein the predetermined processing further comprises at least one of removing an organic material from one of the samples drawn from the supply, or converting a different specie of the predetermined metal present in the one of the samples drawn from the supply to the specific chemical specie; and
   wherein the method further comprises using a control mechanism to control the extraction mechanism, the measurement device, the processing subsystem and the transfer mechanism on an sequential, automated basis, to obtain at least two measurements of the concentration of the specific chemical specie including measurements with and without the predetermined processing respectively.

13. The method of claim 12, wherein the predetermined metal is selenium and wherein the specific chemical specie comprises Se(IV).

14. The method of claim 13, wherein the measurement device comprises a voltametric system with a renewable mercury electrode and a cleaning mode in which the voltametric system is to extract amalgam from the renewable mercury electrode.

15. The method of claim 12, wherein the different specie comprises Se(VI).

16. The method of claim 12, wherein the predetermined metal comprises an element from the group of alkali metals, transition metals, non-metals, metalloids and rare earth elements.

17. The method of claim 12, wherein the predetermined metal comprises an element from the group of selenium, cadmium, lead, copper, arsenic, chromium, beryllium, aluminum, nickel, uranium, selenium and zinc.

18. The method of claim 12, wherein using the control system comprises computing a value representing selection of a treatment chemical to be applied to a liquid drawn from the supply in order to treat the supply, the value dependent on a measurement of the at least two measurements, and outputting a result representing the value.

19. The method of claim 12, wherein using the control system comprises computing a value representing selection of a quantity of a treatment chemical to be applied to a liquid drawn from the supply in order to treat the supply, the value dependent on a measurement of the at least two measurements, and outputting a result representing the value.

20. The method of claim 12, wherein the predetermined metal is selenium, wherein applying the predetermined processing includes each of processing organoselenium from one of the samples drawn from the supply to convert the organoselenium to an inorganic form, and converting the inorganic form to Se(IV) for one of the samples drawn from the supply.

21. The method of claim 12, wherein applying the predetermined processing includes each of heating one of the samples drawn from the supply and introducing an acid to the one of the samples drawn from the supply to mineralize one or more species of the predetermined metal.

22. The method of claim 12, wherein the aqueous matrix comprises waste water.

* * * * *